US009949703B2

(12) United States Patent
Dirisio et al.

(10) Patent No.: US 9,949,703 B2
(45) Date of Patent: Apr. 24, 2018

(54) EXTREMITY IMAGING APPARATUS

(71) Applicant: Carestream Health, Inc., Rochester, NY (US)

(72) Inventors: Anthony Dirisio, Rochester, NY (US); Joseph E. Stagnitto, Conesus, NY (US); Michael A. Litzenberger, Rochester, NY (US); William C. Wendlandt, Rush, NY (US); Peter A. Newman, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 145 days.

(21) Appl. No.: 15/069,010

(22) Filed: Mar. 14, 2016

(65) Prior Publication Data

US 2016/0270747 A1    Sep. 22, 2016

Related U.S. Application Data

(60) Provisional application No. 62/134,256, filed on Mar. 17, 2015.

(51) Int. Cl.
*A61B 6/00* (2006.01)
*A61B 6/03* (2006.01)

(52) U.S. Cl.
CPC ............ *A61B 6/4441* (2013.01); *A61B 6/035* (2013.01); *A61B 6/4085* (2013.01); *A61B 6/4405* (2013.01); *A61B 6/4452* (2013.01); *A61B 6/4476* (2013.01); *A61B 6/50* (2013.01)

(58) Field of Classification Search
CPC ..... A61B 6/035; A61B 6/4085; A61B 6/4405; A61B 6/4441; A61B 6/4452; A61B 6/4476; A61B 6/50
See application file for complete search history.

(56) References Cited

U.S. PATENT DOCUMENTS

| 4,741,015 A | 4/1988 | Charrier |
| 6,580,777 B1 | 6/2003 | Ueki et al. |
| 8,210,745 B2 * | 7/2012 | Yorkston ................ A61B 6/032 378/196 |
| 2004/0022350 A1 | 2/2004 | Gregerson et al. |
| 2008/0056440 A1 | 3/2008 | Fischer et al. |

(Continued)

FOREIGN PATENT DOCUMENTS

| DE | 198 46 980 | 10/1999 |
| DE | 101 47 157 | 4/2003 |

(Continued)

OTHER PUBLICATIONS

International Search Report for International Application No. PCT/US2013/063670 dated Dec. 10, 2013, 2 pages.

(Continued)

*Primary Examiner* — Mark R Gaworecki

(57) ABSTRACT

An x-ray imaging apparatus revolves a digital radiation detector and a radiation source about an imaging area where a subject is positioned to be imaged. A housing encloses the source and the detector, and includes an open housing gap to allow movement of the subject into the imaging area by moving through the open gap. A housing extension may be deployed to close the housing gap and to enclose the detector as it revolves. Shielding assemblies prevent exterior access into the housing.

20 Claims, 39 Drawing Sheets

(56) References Cited

U.S. PATENT DOCUMENTS

| | | |
|---|---|---|
| 2008/0245972 A1 | 10/2008 | Drapeau |
| 2010/0278300 A1 | 11/2010 | Yorkston et al. |
| 2010/0329534 A1 | 12/2010 | Biermann et al. |
| 2011/0210261 A1 | 9/2011 | Maurer, Jr. |
| 2011/0228901 A1 | 9/2011 | Yorkston et al. |
| 2011/0280364 A1 | 11/2011 | Maschke |

FOREIGN PATENT DOCUMENTS

| | | |
|---|---|---|
| DE | 10 2005 013 832 | 8/2006 |
| DE | 10 2008 019 646 | 10/2009 |
| EP | 0 119 660 | 9/1984 |
| EP | 1016375 | 12/1999 |
| EP | 0 676 911 | 9/2000 |
| EP | 0 919 187 | 1/2005 |
| EP | 2127696 | 3/2009 |
| JP | 07-023942 | 1/1995 |
| JP | 2001-269332 | 10/2001 |
| JP | 2003-088523 | 3/2003 |
| JP | 2010-154992 | 7/2010 |
| JP | 2010-200929 | 9/2010 |
| JP | 2013-066784 | 4/2013 |
| WO | 95/21570 | 8/1995 |
| WO | 95/22241 | 8/1995 |
| WO | 95/31936 | 11/1995 |
| WO | 03/070101 | 8/2003 |
| WO | 2010/078481 | 7/2010 |
| WO | 2011/156526 | 12/2011 |

OTHER PUBLICATIONS

International Search Report for International Application No. PCT/US2013/063673 dated Feb. 14, 2014, 7 pages.

International Search Report for International Application No. PCT/US2013/063666 dated Feb. 7, 2014, 6 pages.

International Search Report for International Application No. PCT/US2013/063662 dated Feb. 27, 2014, 6 pages.

\* cited by examiner

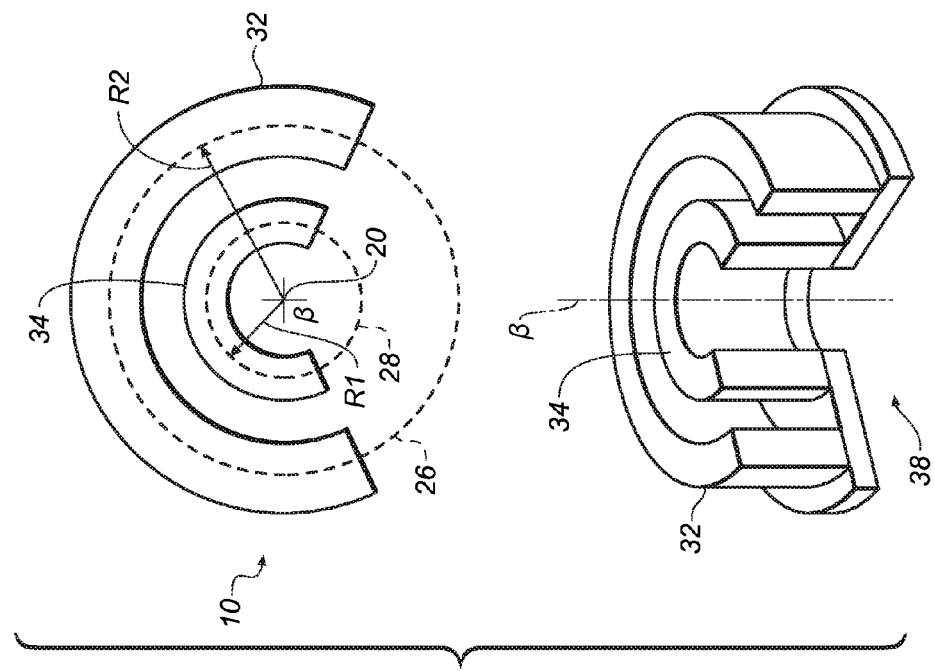
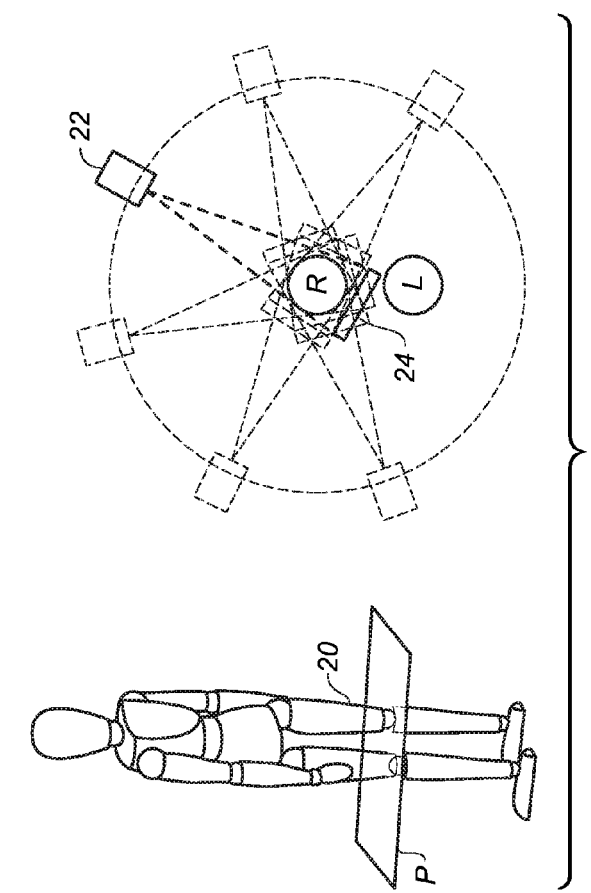
FIG. 1
FIG. 2

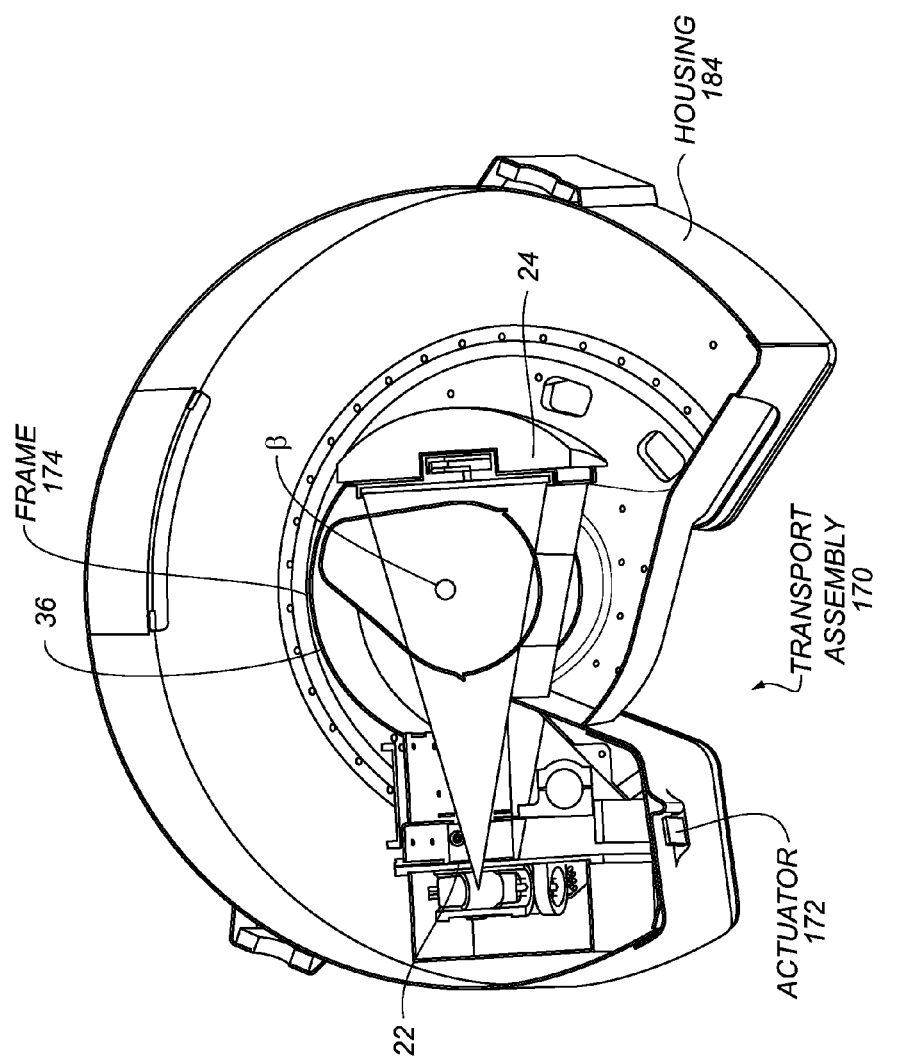

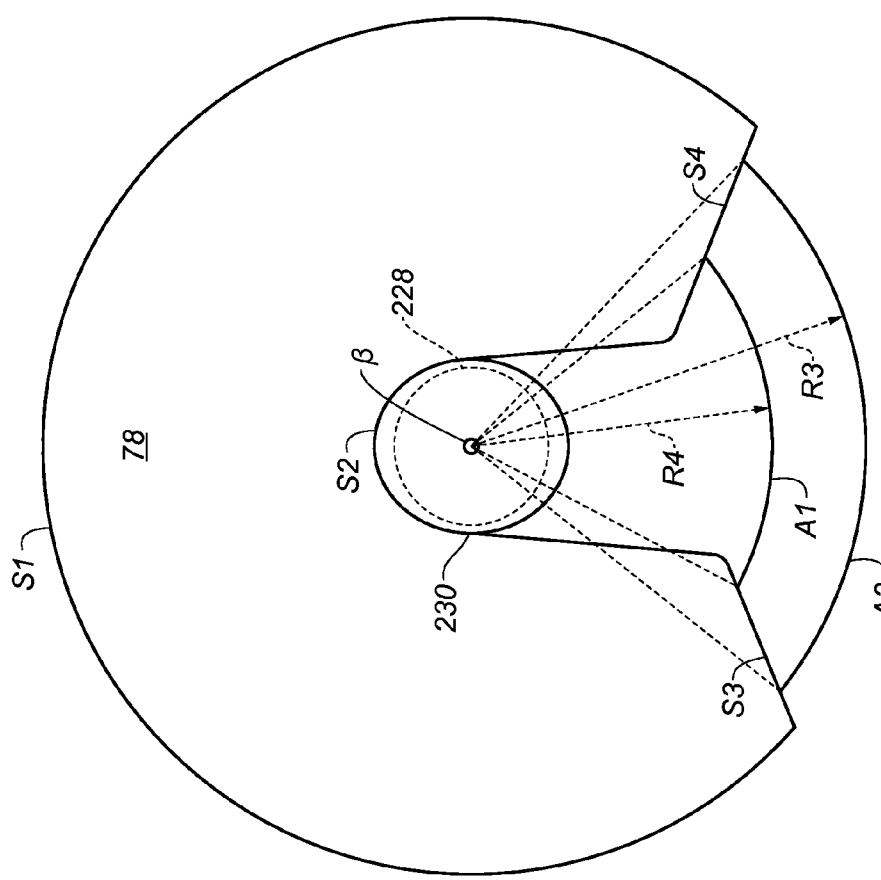

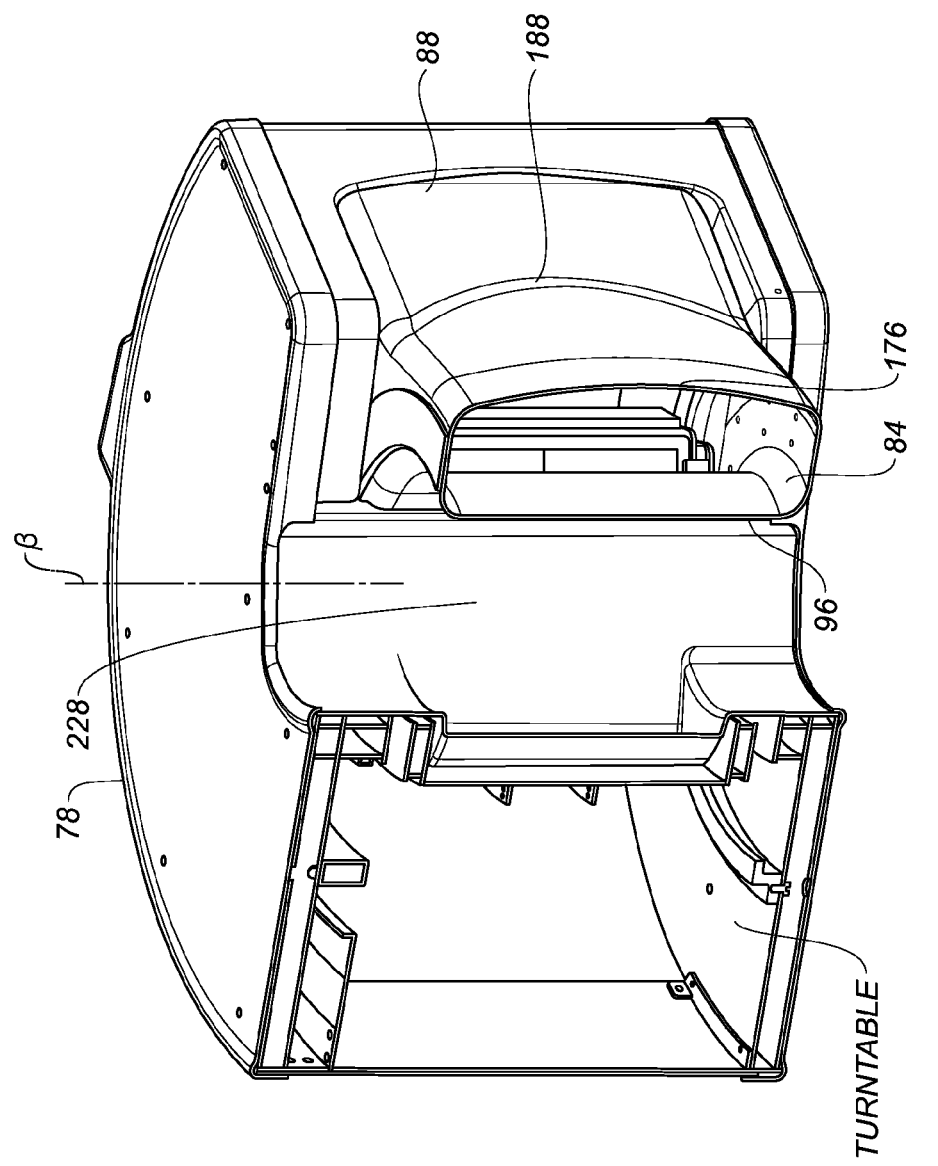

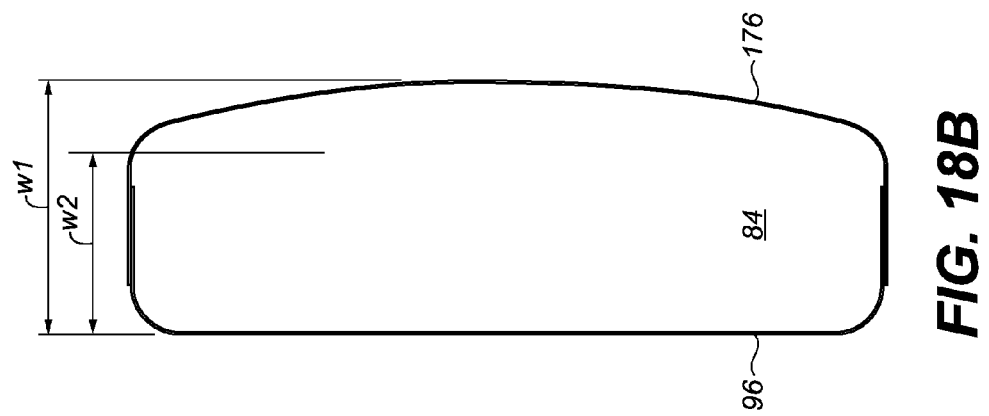

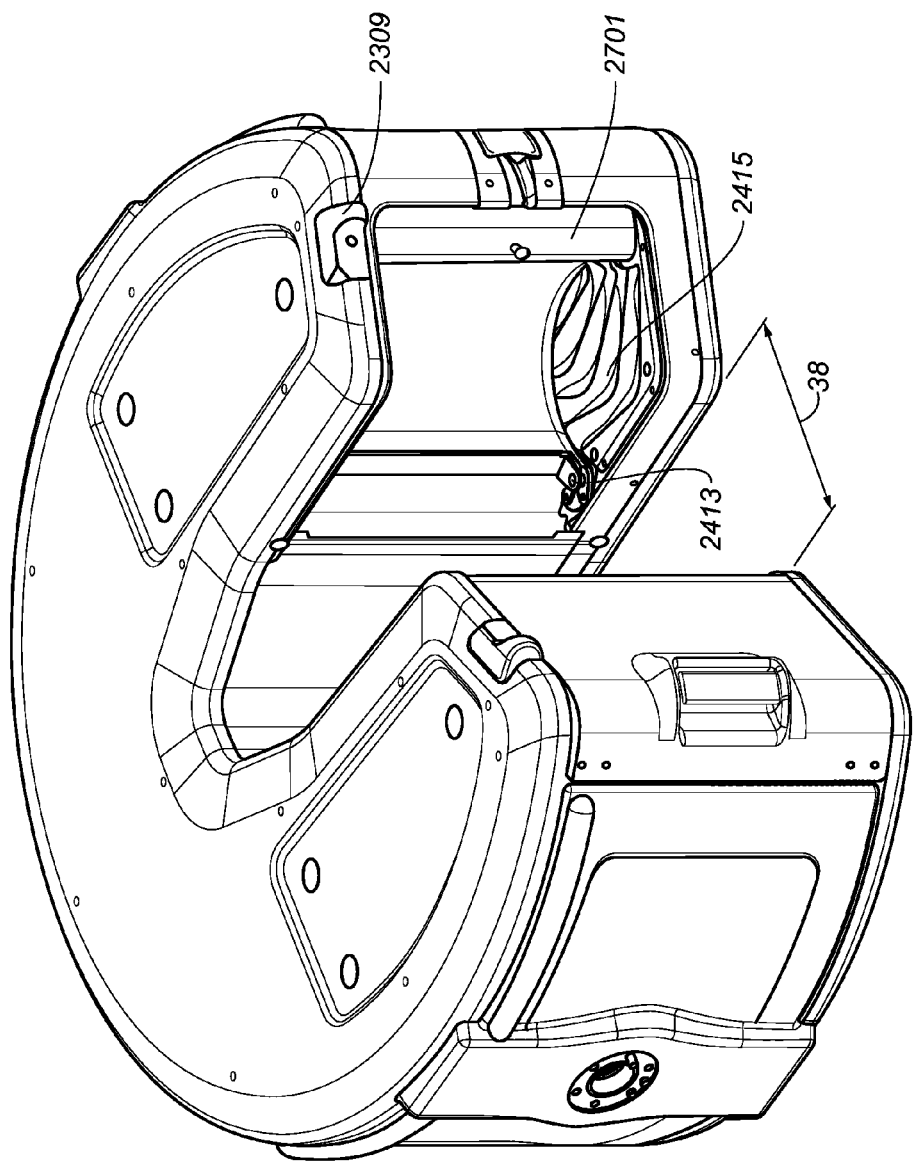

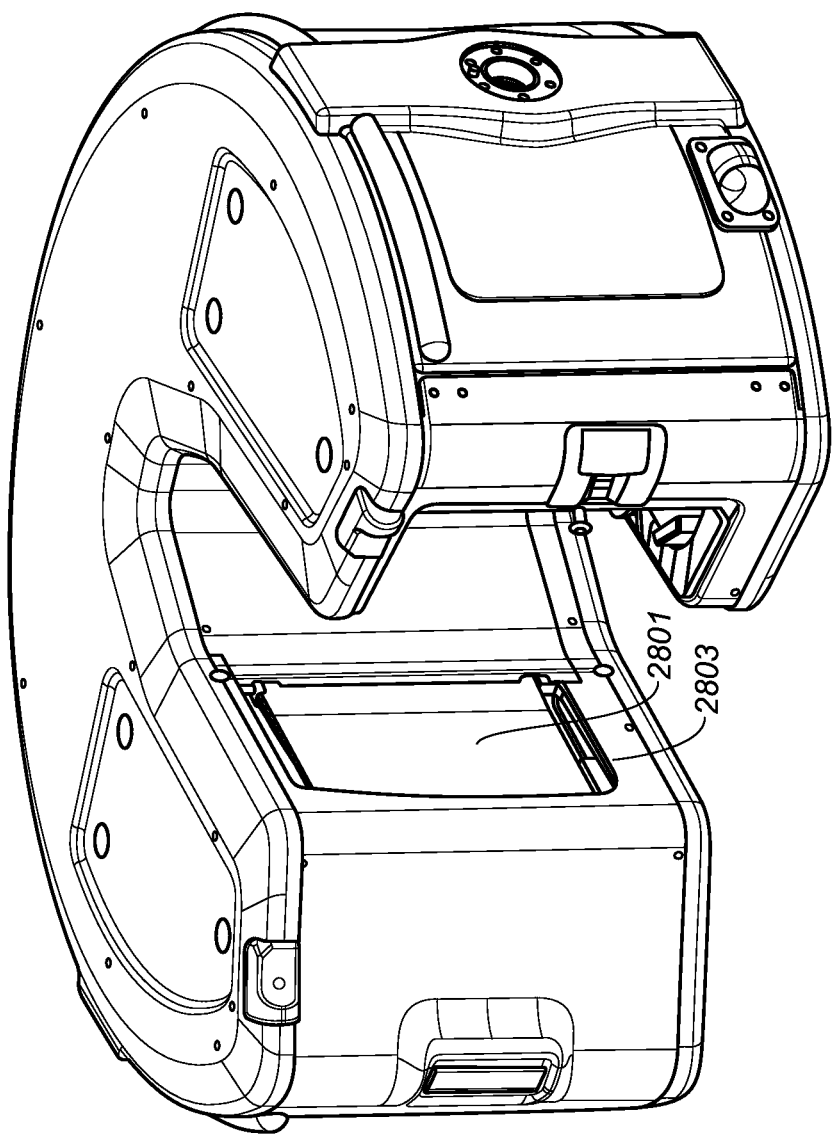

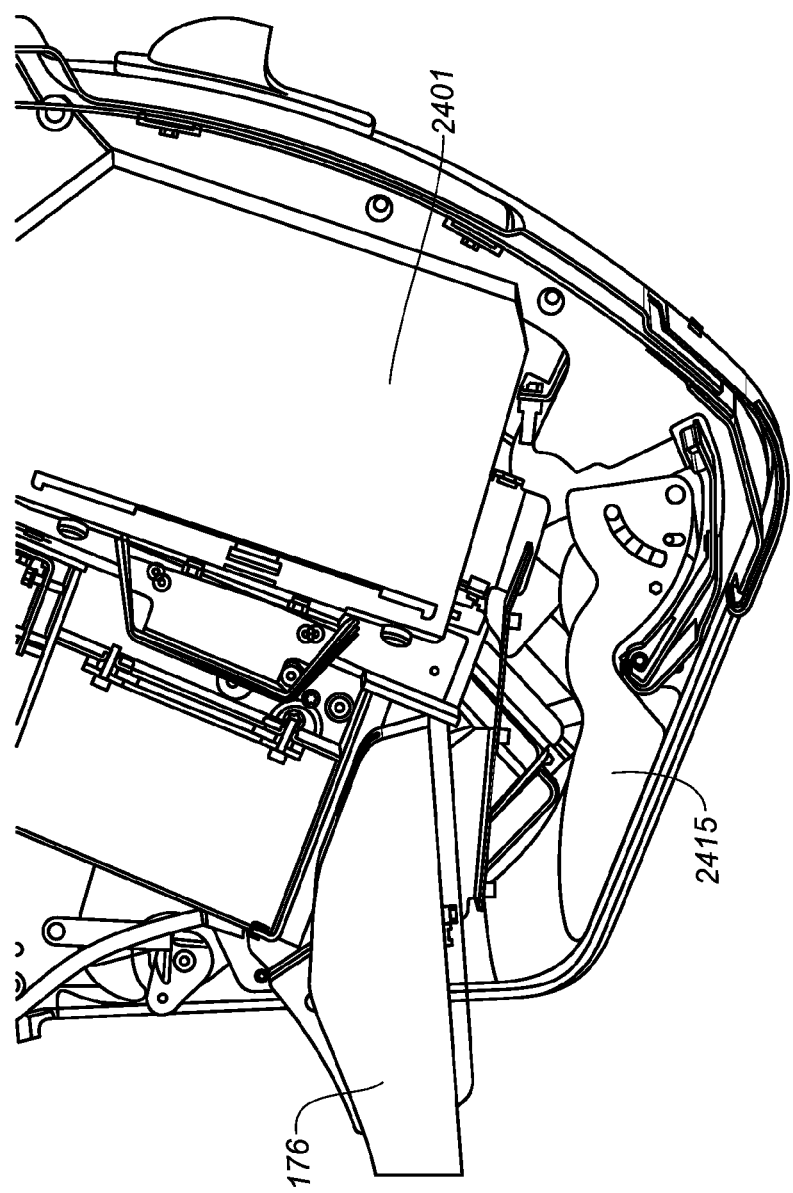

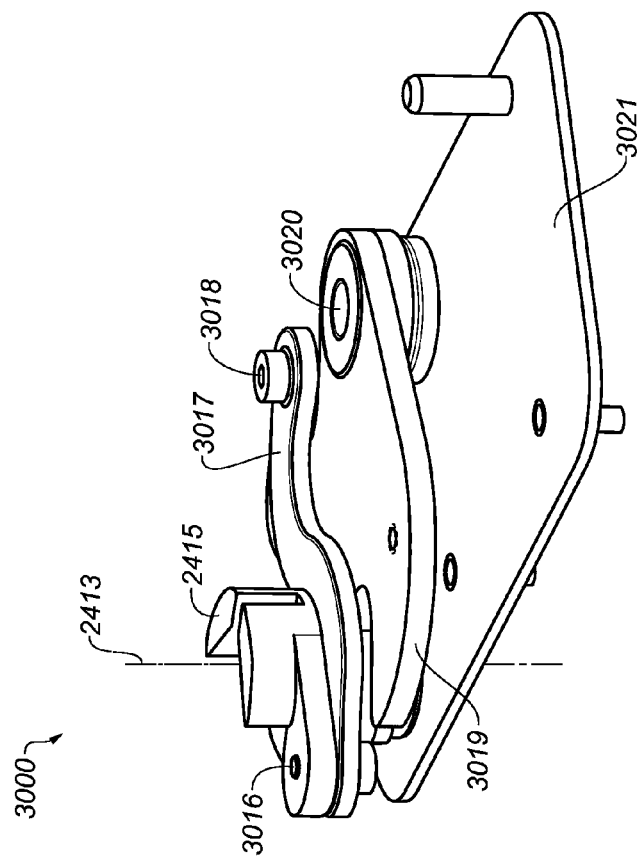
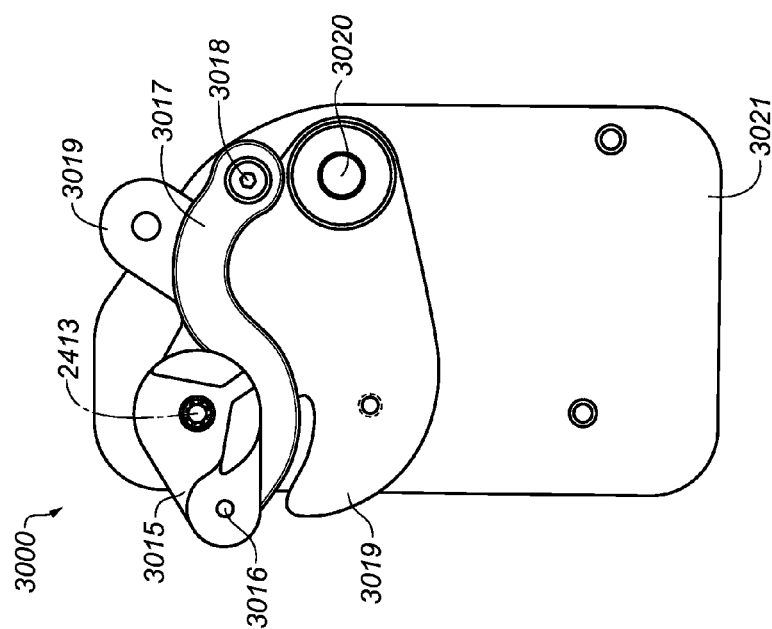
FIG. 30B
FIG. 30A

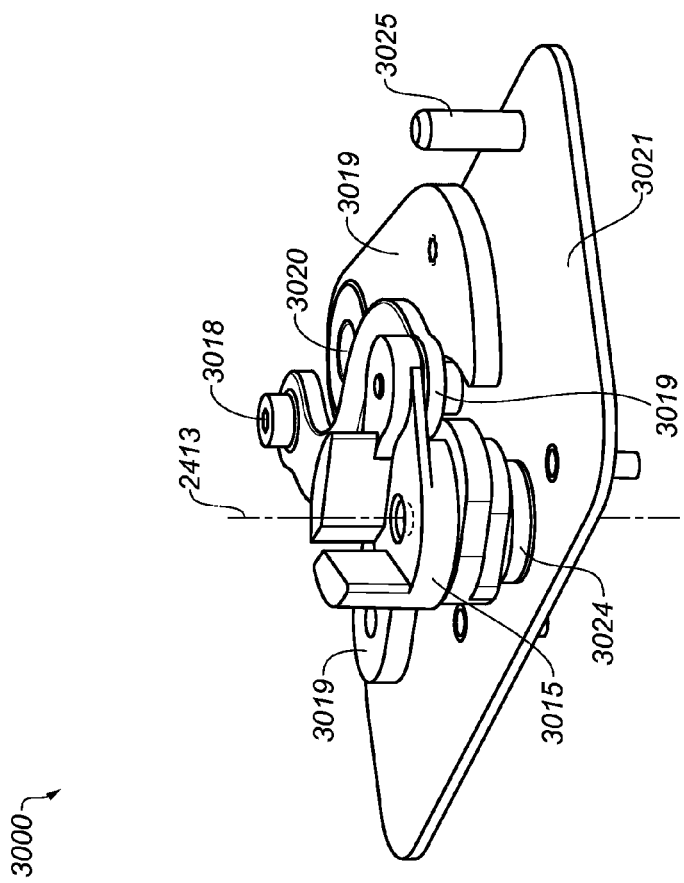
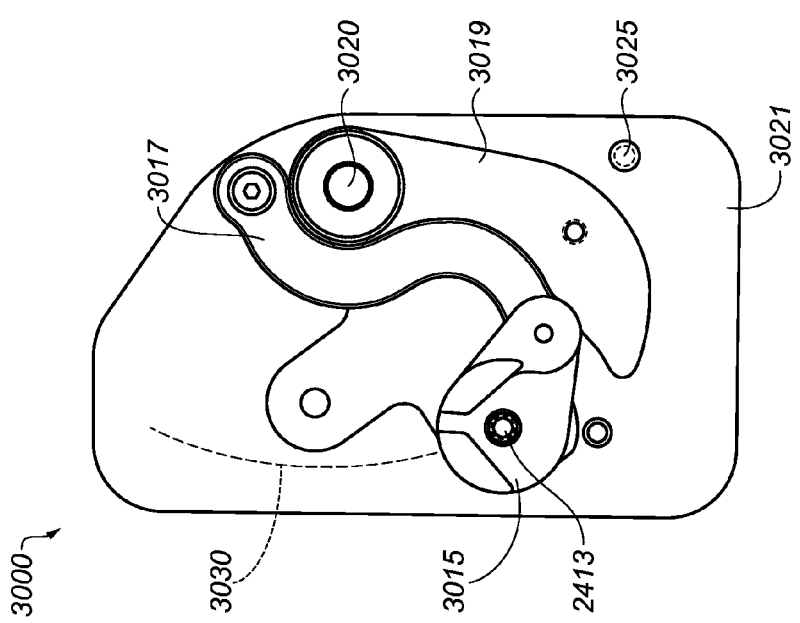
FIG. 30F
FIG. 30E

EXTREMITY IMAGING APPARATUS

CROSS REFERENCE TO RELATED APPLICATIONS

This application claims priority to U.S. Patent Application Ser. No. 62/134,256, filed Mar. 17, 2015, in the name of Dirisio et al., and entitled EXTREMITY IMAGING APPARATUS, which is incorporated herein by reference in its entirety.

FIELD OF THE INVENTION

The invention relates generally to diagnostic imaging and in particular to cone beam imaging systems used for obtaining volume images of extremities.

BACKGROUND OF THE INVENTION

3-D volume imaging has proved to be a valuable diagnostic tool that offers significant advantages over earlier 2-D radiographic imaging techniques for evaluating the condition of internal structures and organs. 3-D imaging of a patient or other subject has been made possible by a number of advancements, including the development of high-speed imaging detectors, such as digital radiography (DR) detectors that enable multiple images to be taken in rapid succession.

Cone beam computed tomography (CBCT) or cone beam CT technology offers considerable promise as one type of diagnostic tool for providing 3-D volume images. Cone beam CT systems capture volumetric data sets by using a high frame rate digital radiography (DR) detector and an x-ray source, typically affixed to a gantry that rotates about the object to be imaged, directing, from various points along its orbit around the subject, a divergent cone beam of x-rays toward the subject. The CBCT system captures projections throughout the rotation, for example, one 2-D projection image at every degree of rotation. The projections are then reconstructed into a 3D volume image using various techniques. Among well known methods for reconstructing the 3-D volume image from the 2-D image data are filtered back projection approaches.

Although 3-D images of diagnostic quality can be generated using CBCT systems and technology, a number of technical challenges remain. In some cases, for example, there can be a limited range of angular rotation of the x-ray source and detector with respect to the subject. CBCT Imaging of legs, arms, and other extremities can be hampered by physical obstruction from a paired extremity. This is an obstacle that is encountered in obtaining CBCT image projections for the human leg or knee, for example. Not all imaging positions around the knee are accessible; the patient's own anatomy often prevents the radiation source and image detector from being positioned over a portion of the scan circumference.

To illustrate the problem faced in CBCT imaging of the knee, the top view of FIG. 1 shows the circular scan paths for a radiation source 22 and detector 24 when imaging the right knee R of a patient as a subject 20. Various positions of radiation source 22 and detector 24 are shown in dashed line form. Source 22, placed at some distance from the knee, can be positioned at different points over an arc of about 200 degrees; with any larger arc the paired extremity, left knee L, blocks the way. Detector 24, smaller than source 22 and typically placed very near subject 20, can be positioned between the patient's right and left knees and is thus capable of positioning over the full circular orbit. The scan path of the source and/or detector may define a source and/or detector plane P through which the source and/or detector travel as they traverse respective source and detector paths around a region of the subject 20.

A full 360 degree orbit of the source and detector is not needed for conventional CBCT imaging; instead, sufficient information for image reconstruction can be obtained with an orbital scan range that just exceeds 180 degrees by the angle of the cone beam itself, for example. However, in some cases it can be difficult to obtain much more than about 180 degree revolution for imaging the knee or other joints. Moreover, there can be diagnostic situations in which obtaining projection images over a certain range of angles has advantages, but patient anatomy blocks the source, detector, or both from imaging over that range. Some of the proposed solutions for obtaining images of extremities under these conditions require the patient to assume a position that is awkward or uncomfortable. The position of the extremity, as imaged, is not representative of how the limb or other extremity serves the patient in movement or under weight-bearing conditions. It can be helpful, for example, to examine the condition of a knee or ankle joint under the normal weight load exerted on that joint by the patient as well as in a relaxed position. But, if the patient is required to assume a position that is not usually encountered in typical movement or posture, there may be excessive strain, or insufficient strain, or poorly directed strain or tension, on the joint. The knee or ankle joint, under some artificially applied load and at an angle not taken when standing, may not behave exactly as it does when bearing the patient's weight in a standing position. Images of extremities under these conditions may fail to accurately represent how an extremity or joint is used and may not provide sufficient information for assessment and treatment planning.

Still other difficulties with conventional solutions for extremity imaging relate to poor image quality. For image quality, the CBCT sequence requires that the detector be positioned close to the subject and that the source of the cone beam radiation be at a sufficient distance from the subject. This provides the best image and reduces image truncation and consequent lost data. Positioning the subject midway between the detector and the source, as some conventional systems have done, not only noticeably compromises image quality, but also places the patient too near the radiation source, so that radiation levels are considerably higher.

CBCT imaging represents a number of challenges that also affect other types of volume imaging that employ a radiation source and detector orbiting an extremity over a range of angles. There are various tomographic imaging modes that can be used to obtain depth information for a scanned extremity.

In summary, for extremity imaging, particularly for imaging the lower paired extremities, a number of improvements are needed, including the following:

(i) improved placement of the radiation source and detector relative to the imaged subject to provide acceptable radiation levels and image quality throughout the scanning sequence, with the capability for at least coarse automated setup for examining an extremity under favorable conditions;

(ii) system flexibility for imaging at different heights with respect to the rotational axis of the source and detector, including the flexibility to allow imaging with the patient standing comfortably;

(iii) capability to adjust the angle of the rotational axis to suit patient positioning requirements;

(iv) improved patient accessibility, so that the patient does not need to contort, twist, or unduly stress limbs or joints that may have been injured in order to provide images of those body parts;

(v) improved ergonomics for obtaining the CBCT image, allowing the patient to stand or sit with normal posture, for example. This would also allow load-bearing extremities, such as legs, knees, and ankles, to be imaged under the normal load exerted by the patient's weight, rather than under simulated loading conditions and provide options for supporting the patient; and (vi) adaptability for multi-use imaging, allowing a single imaging apparatus to be configurable for imaging any of a number of extremities, including knee, ankle, toe, hand, elbow, and other extremities. This also includes the capability to operate the imaging system in different imaging modes, including CBCT, two-dimensional (2-D) projection radiography, fluoroscopy, and other tomography modes.

In summary, the capability for straightforward configuration and positioning of the imaging apparatus allows the advantages of CBCT imaging to be adaptable for use with a range of extremities, to obtain volume images under a suitable imaging modality, with the image extremity presented at a suitable orientation under both load-bearing and non-load-bearing conditions, and with the patient appropriately standing or seated.

SUMMARY OF THE INVENTION

An x-ray imaging apparatus revolves a digital radiation detector and a radiation source about an imaging area where a subject is positioned to be imaged. A housing encloses the source and the detector, and includes an open housing gap to allow movement of the subject into the imaging area by moving through the open gap. A housing extension may be deployed to close the housing gap. Shielding assemblies prevent exterior access into the housing.

In one embodiment, an apparatus for cone beam computed tomographic imaging includes a digital radiation detector and a radiation source configured to revolve about a central imaging axis where a portion of an extremity of a patient is positioned. A C-shaped housing encloses the source and the detector but has a housing gap to allow patient entry. A housing extension attached to the housing extends from the housing to close the housing gap and surround the extremity. Means for shielding an interior of the housing from exterior access is provided proximate the housing extension.

In another embodiment, an apparatus for x-ray imaging has a digital radiation detector and a radiation source configured to travel about an imaging area where an object is positioned for imaging. A housing encloses the source and the detector, and has an open housing gap to allow movement of the object into the imaging area. A housing extension is designed to extend from the housing to close the housing gap. A shield prevents access to an interior of the housing from outside the housing proximate the housing extension.

In another embodiment, an apparatus for cone beam computed tomographic imaging of an extremity of a patient includes a digital radiation detector and a radiation source. A detector mechanism attached to the detector moves the detector along a detector path while a source mechanism attached to the source moves the source along a source path. The detector path is generally centered about a central imaging axis, as is the source path. A distance of the detector path to the central axis is shorter than a distance from the source path to the central axis. The extremity of the patient is properly positioned at or proximate the central imaging axis to be imaged by the apparatus. A C-shaped encloses the source, the source mechanism, the detector, and the detector mechanism. A housing gap allows the extremity of the patient to be positioned at the central imaging axis by moving at least a portion of the extremity through the housing gap. A housing extension attached to the housing is configured to be controllably deployed across the housing gap to enclose the detector as the detector moves across the housing gap. A shield assembly prevents access to an interior of the housing when the extension is deployed or retracted.

It is another aspect of this application to provide apparatus and/or method embodiments that provide a door, or scanner housing extension, to close a peripheral gap, or a housing gap, in a scanner apparatus that has a C-shape or C-cross-sectional shape.

It is another aspect of this application to provide apparatus and/or method embodiments that provide a door, or scanner housing extension, to close a peripheral gap, or a housing gap, in a scanner apparatus that has a C-shape or C-cross-sectional shape whereby the door is capable of appropriately pivoting open to clear the housing gap so that a patient extremity may be positioned at an examining axis of the apparatus.

It is another aspect of this application to provide apparatus and/or method embodiments that provide a door, or scanner housing extension, having sufficient interior clearance, as in a hollow configuration, to enclose at least one of the source and detector as it travels across the housing gap, or peripheral gap, during movement along the source/detector transport path.

In one embodiment, a scanner housing defines a radially extending circumferential opening from an inner longitudinal axis to a radially outer circumferential surface of the housing, where the radially extending circumferential opening extends from a lower surface to an upper surface of the housing. In one embodiment, a door can be configured to reciprocally move between a first position and a second position, where in the first position the door is positioned to extend across and enclose a portion of the circumferential gap, and where in the second position the door is positioned to clear the portion of the circumferential gap, where the support column extends from a support base. In one embodiment, the door can include a closure portion that covers a gap in the scanner housing at least following door closing, wherein the door has a cylindrical surface facing the inner wall of the housing.

In one embodiment, a CBCT apparatus can include a support structure; a scanner assembly coupled to the support structure, the scanner housing to enclose at least a portion of a scanner comprising a radiation source and detector configured to rotate at least 180 degrees with a prescribed spatial relationship within the scanner housing; a first device configured to move the scanner assembly along a vertical direction of the support column; a second device configured to revolve the scanner assembly to a vertical or other angular orientation; and a third device configured to orient the scanner assembly by revolving the scanner assembly about a different axis.

It is another aspect of this application to provide apparatus and/or method embodiments that provide a door, or scanner housing extension, to close a peripheral gap, or a housing gap, in a scanner apparatus that has a C-shape or C-cross-sectional shape whereby the interior space of the scanner housing is shielded to access from an exterior of the housing and is blocked from view or visibility to the exterior.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications. The drawings below are intended to be drawn neither to any precise scale with respect to relative size, angular relationship, relative position, or timing relationship, nor to any combinational relationship with respect to interchangeability, substitution, or representation of a required implementation.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 1 is a schematic view showing the geometry and limitations of CBCT scanning for portions of the lower leg.

FIG. 2 shows a top and perspective view of the scanning pattern for an imaging apparatus according to an embodiment of the application.

FIG. 8 is a perspective view of the scanner components of an extremity imaging apparatus according to an embodiment of the application.

FIG. 17B is a top view of the imaging scanner with internal imaging components and central arc angles shown.

FIG. 18A is a cutaway view that shows the hollow door in position within the scanner housing, whereby the hollowed out door includes sufficient room for the detector to pass therethrough.

FIG. 18B is an outline view of the door showing width tapering.

FIG. 27 is a partial transparent perspective diagram of the scanner apparatus with the housing extension open.

FIG. 28 is another partial transparent perspective diagram of the scanner apparatus with the housing extension open.

FIG. 29B is a cross-section diagram of a portion of the scanner apparatus at the door attachment area with the source assembly at or near a terminal position of the source path.

FIGS. 30A-30B are diagrams that show an embodiment of the hinge mechanism for opening and closing the housing extension where the housing extension is in a closed position.

FIGS. 30E-30F are diagrams that shows the embodiment of the hinge mechanism of FIG. 30A-30B where the housing extension is in an open position.

DETAILED DESCRIPTION OF EXEMPLARY EMBODIMENTS

Figure 3C:
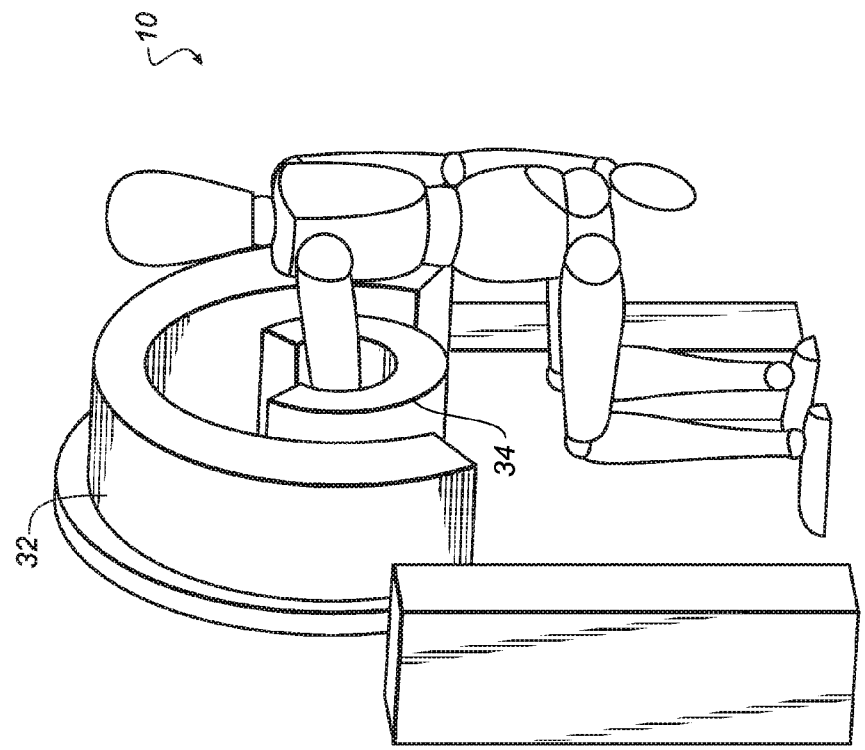
FIG. 3C is a perspective view showing patient access to another imaging apparatus according to an embodiment of the application.

The perspective and corresponding top view of FIG. 2 show how the scanning pattern is provided for components of CBCT imaging apparatus 10 according to one embodiment. A detector path 28, shaped as a circular arc of a suitable radius R1 from a central axis β is provided for a digital radiation detector by a detector transport mechanism 34. A source path 26 shaped as a circular arc of a second, larger radius R2 is provided for a radiation source by a source transport mechanism 32. In one embodiment, a non-linear source path 26 is greater in length than a non-linear detector path 24. According to an embodiment of the application, described in more detail subsequently, the same C-shaped transport system provides both detector transport 34 and source transport 32. The extremity of subject 20 is preferably substantially centered along central axis β so that central axis β can be considered as a line through points in the extremity of subject 20. In one embodiment, an imaging bore of the CBCT apparatus can include or encompass the central axis β. The limiting geometry for image capture is due to the arc of source transport 32 blocked by patient anatomy, such as by a paired limb), and thus limited typically to less than about 220 degrees, as noted previously. The circumferential gap, or opening, or housing gap, or peripheral gap 38 exists between the endpoints of the arc of source path 26, between ends of a C-shaped transport mechanism, or between ends of a C-shaped scanner housing as described herein. Gap or opening 38 provides space for the patient to stand, for example, while one leg is being imaged. It also provides access through the gap for positioning a patient extremity by moving the patient extremity through the gap in a direction substantially perpendicular to the axis β without requiring the patient to insert his or her extremity through one end of the bore opening.

Figure 3A:
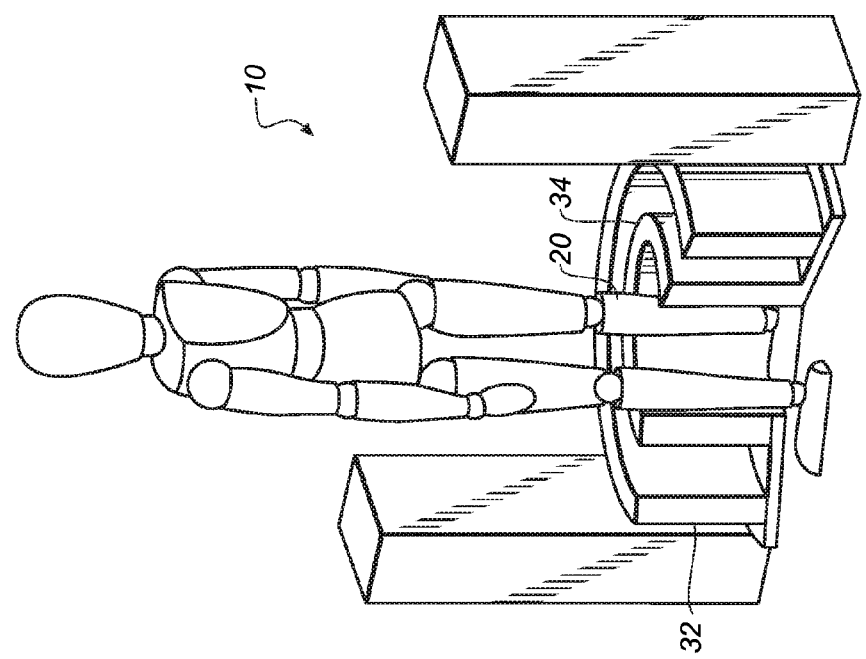
FIG. 3A is a perspective view showing patient access to an imaging apparatus according to an embodiment of the application.
Figure 3B:
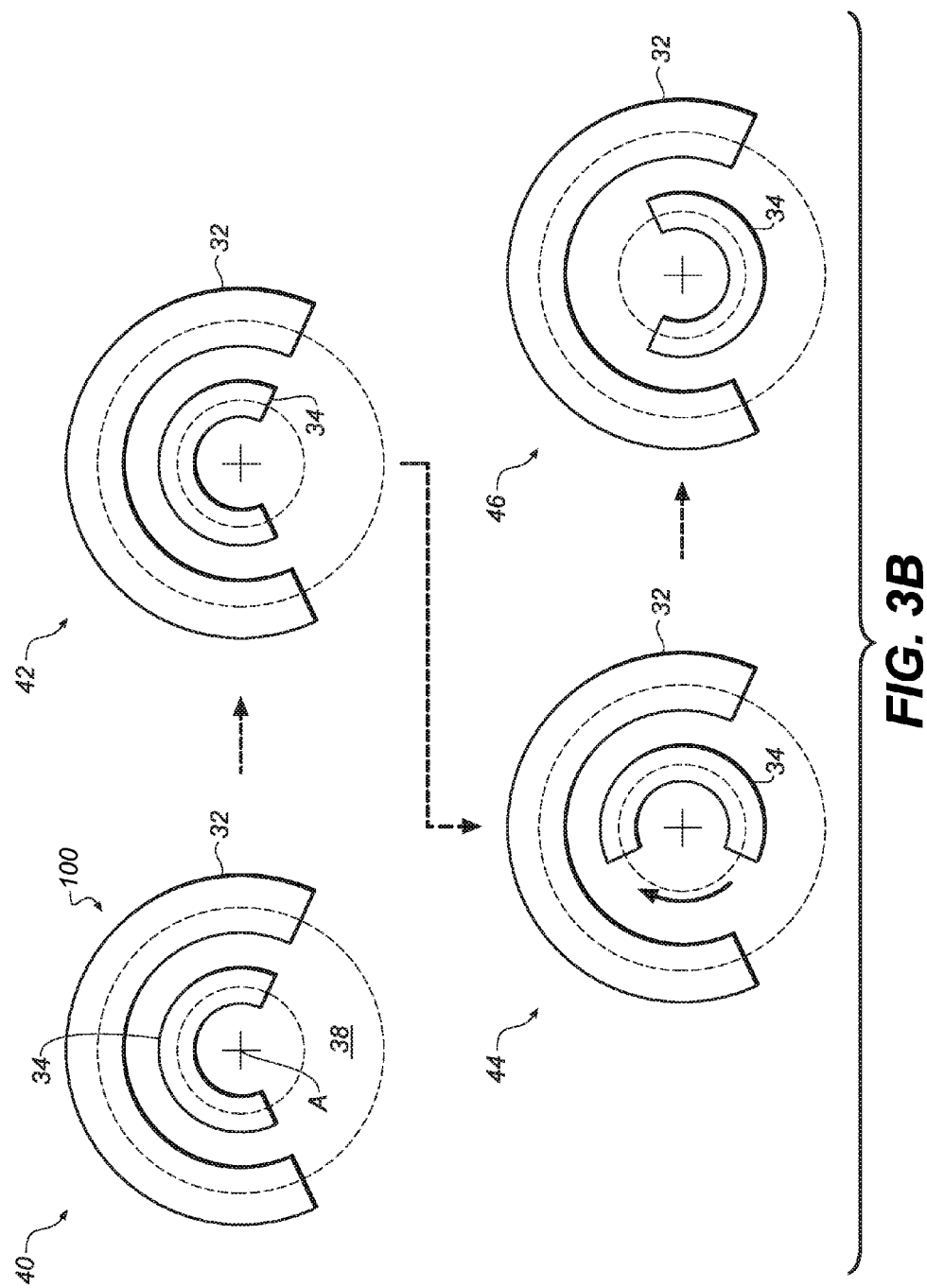
FIG. 3B is a top view showing a sequence of steps for enclosing the extremity to be imaged within the path of the detector transport.

Detector path 28 can extend across housing gap 38 to allow scanning, since the detector is not necessarily blocked by patient anatomy and can have a detector travel path extending between a patient's extremities and at least partially around an imaged extremity. Embodiments of the present invention allow clearance of the housing gap by moving away a housing extension, or door, and scanning components, as explained herein, to allow access for the patient as part of initial patient positioning. The perspective view in FIG. 2, for example, shows detector transport 34 rotated to open up circumferential gap 38. With reference to FIG. 3A, detector transport 34 may be translated to the open position, as shown in FIG. 3A, and the patient can freely move in and out of position for imaging with reference to the imaging axis β. When the patient is properly in position, detector transport 34 is revolved about axis β by more than 180 degrees; according to an embodiment of the invention, detector transport 34 is revolved about axis β by substantially 200 degrees. This patient access and subsequent adjustment of detector transport 34 is shown in successive stages in FIG. 3B. This orbital movement confines the extremity to be imaged more effectively and places detector 24, not visible in FIGS. 2-3B due to the detector transport 34 housing, in position near subject 20 for obtaining the first projection image in sequence. In one embodiment described herein, a detector transport 34 can include shielding, a housing extension, a door, or a combination thereof, over part of the detector path, and/or the gap 38.

Circumferential gap or opening 38 not only allows access for positioning of a subject's leg or other extremity, but also allows sufficient space for the patient to stand in normal posture during imaging, placing the subject leg for imaging in the central position along axis β (FIG. 2) and the non-imaged paired leg within the space defined by circumferential gap 38. Circumferential gap or opening 38 extends approximately 360 degrees minus the fan angle (e.g., between ends of the source path or ends of the C-shaped housing), which is determined by source-detector geometry and distance. Circumferential gap or opening 38 permits access for easily positioning the extremity so that it can be centered along central axis β. Once the patient's leg or other extremity is in place, detector transport 34, a hooded cover, hollow door, housing extension, or other member in the transport path, can be revolved into position, enclosing the detector path in the circumferential housing gap or opening 38.

Figure 4:
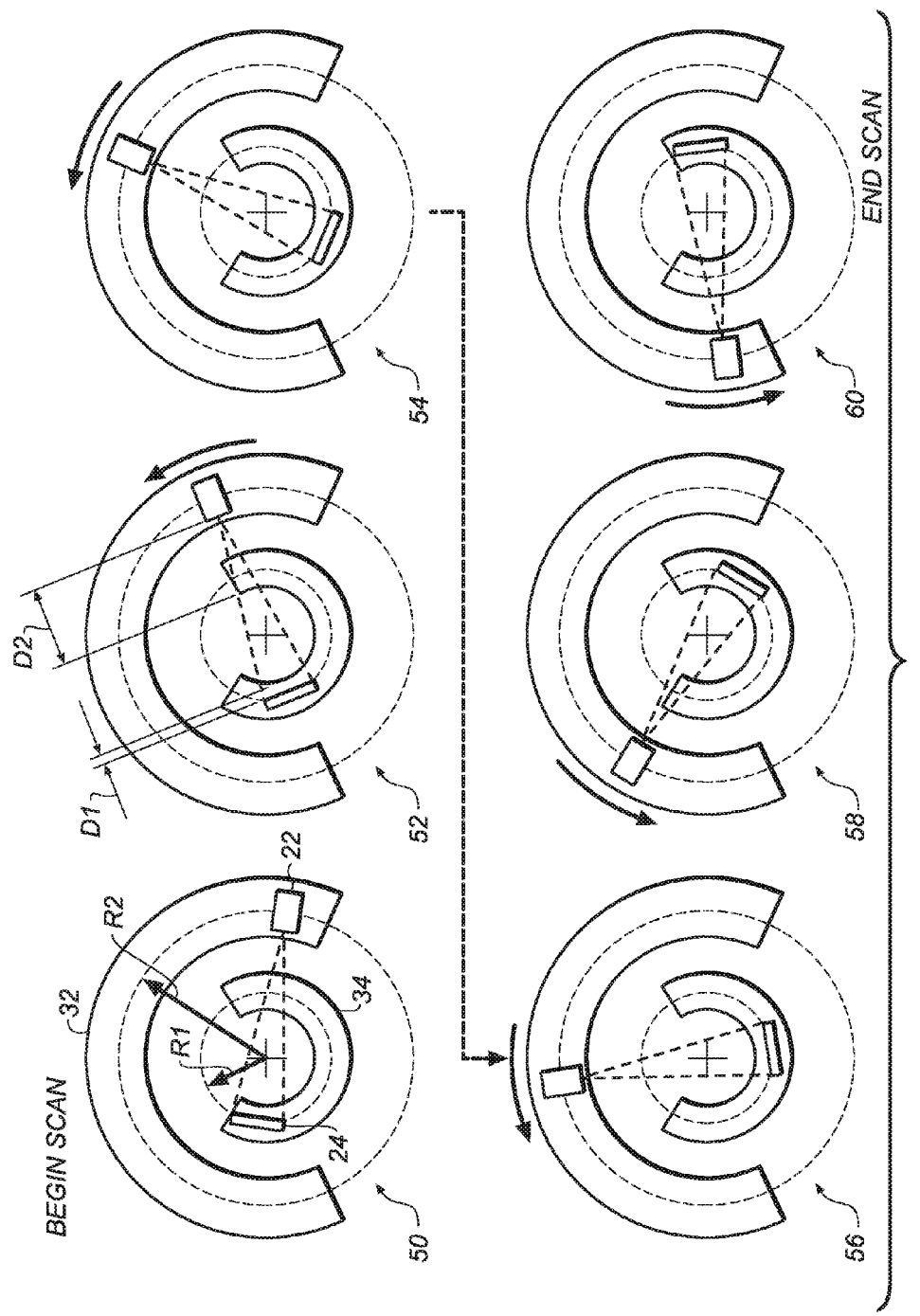
FIG. 4 show portions of the operational sequence for obtaining CBCT projections of a portion of a patient's leg at a number of angular positions when using the imaging apparatus according to an embodiment of the application.

By way of example, the top views of FIG. 4 show portions of the operational sequence for obtaining CBCT projections of a portion of a patient's extremity at a number of angular positions when using the CBCT imaging apparatus 10. The relative positions of radiation source 22 and detector 24, which may be concealed under a hood or chassis, as noted earlier, are shown in FIG. 4. The source 22 and detector 24 can be aligned so the radiation source 22 can direct radiation toward the detector 24 (e.g., diametrically opposite in relation to axis β) at each position during the CBCT scan and projection imaging. The sequence begins at a begin scan position 50, with radiation source 22 and detector 24 at initial positions to obtain an image at a first angle. Then, both radiation source 22 and detector 24 revolve about axis β as represented in interim scan positions 52, 54, 56, and 58. Imaging terminates at an end scan position 60. As this sequence shows, source 22 and detector 24 are in opposing positions relative to axis β at each imaging angle. Throughout the scanning cycle, detector 24 is within a short distance D1 of subject 20. Source 22 is positioned at a longer distance D2 from subject 20. The positioning of source 22 and detector 24 components can be carried out by separate actuators, one for each transport path, or by a single rotatable member, as described in more detail subsequently. It should be noted that scanning motion in the opposite direction, that is, clockwise with respect to the example shown in FIG. 4, is also possible, with the corresponding changes in initial and terminal scan positions.

Figure 5:
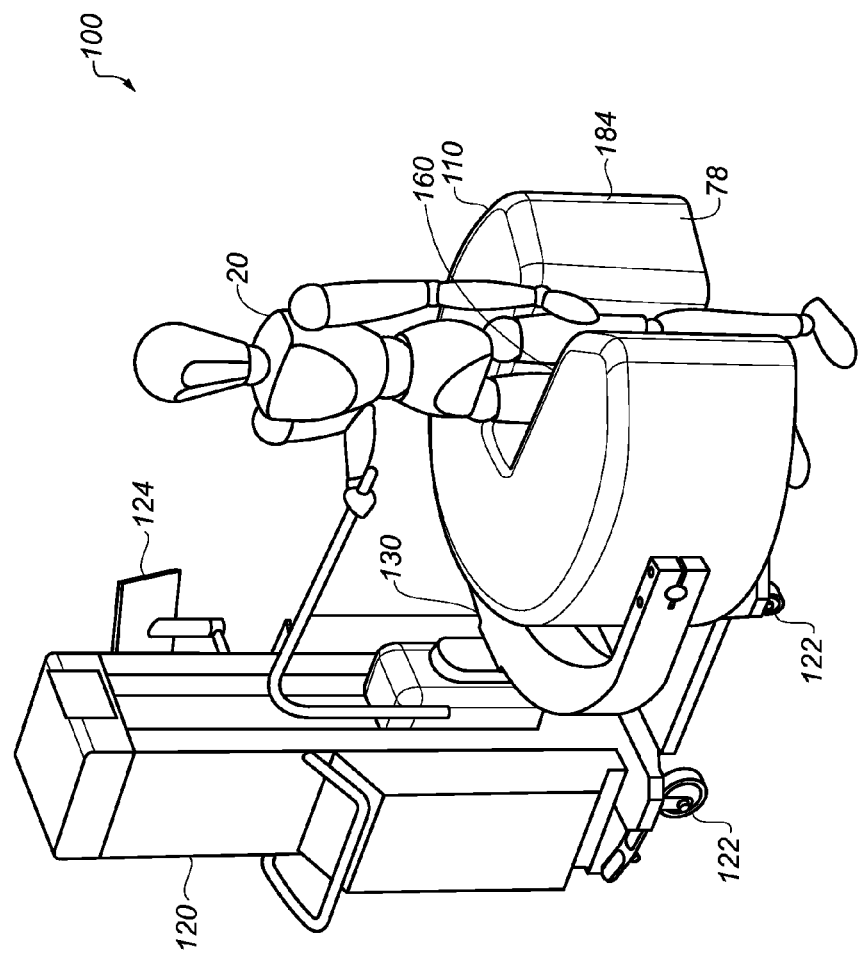
FIG. 5 is a perspective view that shows a CBCT imaging apparatus for extremity imaging according to an embodiment of the application.
Figure 6A:
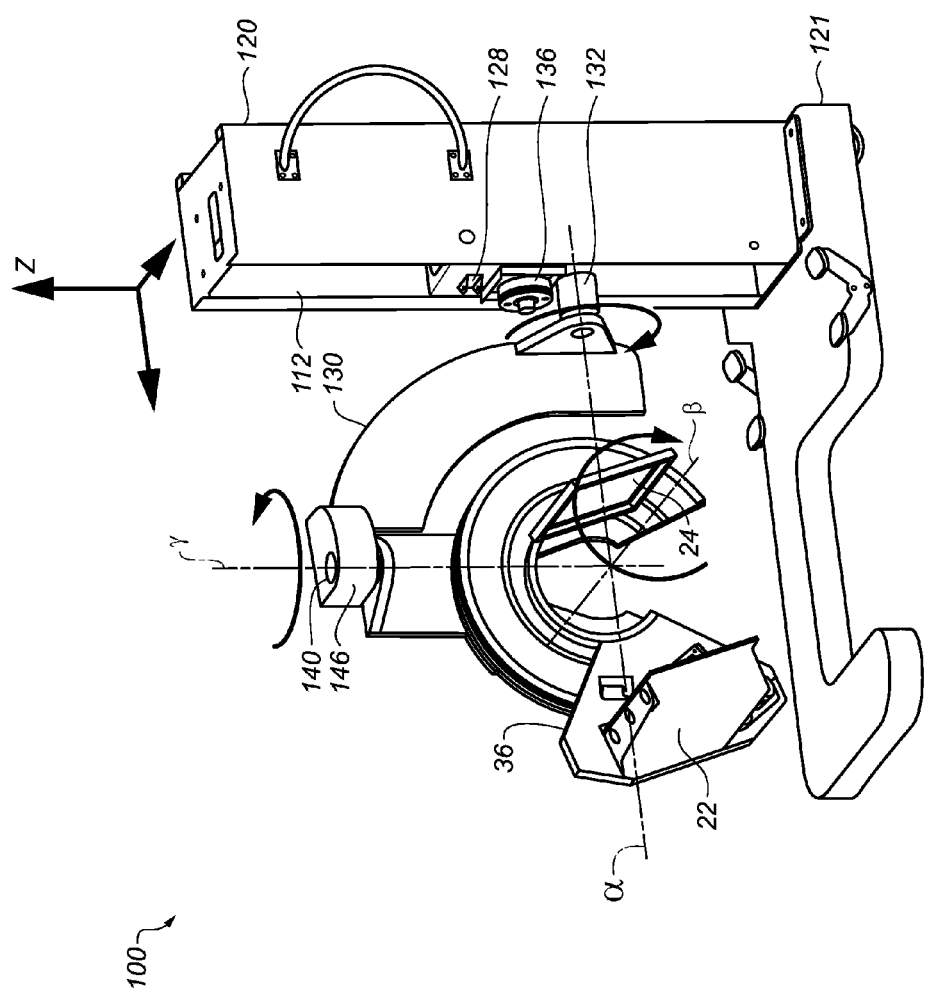
FIG. 6A shows internal components used for imaging ring (or scanner) translation and positioning.

Given this basic operation sequence in which the source 22 and detector 24 orbit the subject extremity, the usefulness of an imaging system that is adaptable for imaging patient extremities with the patient sitting or standing and in load-bearing or non load-bearing postures can be appreciated. The perspective view of FIG. 5 shows a CBCT imaging apparatus 100 for extremity imaging according to an embodiment of the invention. Imaging apparatus 100 has a gimballed imaging, or scanning, apparatus 110 with a housing 78 that conceals source 22 and detector 24 therewithin. Imaging apparatus, or scanner, 110 is adjustable in height and rotatable in gimbaled fashion about non-parallel axes, such as about substantially orthogonal axes, as described in subsequent figures, to adapt to various patient postures and extremity imaging conditions. A support column 120 supports scanner 110 on a yoke, or bifurcated or forked support arm 130, a rigid supporting element that has adjustable height and further provides rotation of scanner 110 as described subsequently. Support column 120 can be fixed in position, such as mounted to a floor, wall, or ceiling. According to portable CBCT embodiments such as shown in FIG. 6A and elsewhere, support column 120 mounts to a support base 121 that also includes optional wheels or casters 122 for transporting and maneuvering imaging apparatus 100 into position. A control panel 124 can provide an operator interface, such as a display monitor, for entering instructions for apparatus 100 adjustment and operation. In one embodiment, the control panel 124 can include a processor or computer (e.g., hardware, firmware and/or software) to control operations of the CBCT system 100. Support column 120 can be of fixed height or may have telescoping operation, such as for improved visibility when apparatus 100 is moved.

FIG. 6A shows portions of exemplary internal imaging and positioning mechanisms (with covers removed) for scanner apparatus 110 that allow imaging apparatus 100 the capability for imaging extremities with a variety of configurations. The α-axis and the γ-axis are non-parallel, to allow gimbaled action. According to an embodiment of the application as shown in FIG. 6A, the α-axis and the γ-axis are mutually orthogonal. The α-axis is substantially orthogonal to the z-axis. The intersection of the α-axis and the γ-axis can be offset from support column 120 by some non-zero distance.

FIG. 6A shows an exemplary embodiment to achieve vertical motion (along the z-axis). Within support column 120, a vertical carriage translation element 128 is actuated in order to travel upwards or downwards along column 120 within a track 112 in a vertical direction. Carriage translation element 128 has a support shaft 132 that is coupled to an actuator 136 for providing α-axis rotation to forked or C-shaped support arm 130. Forked support arm 130, shown only partially in FIG. 6A to allow a better view of underlying components, is coupled to support shaft 132. X-ray source 22 and receiver 24 are mounted on a rotatable gantry 36 for rotation about a scan or central axis, designated as the β axis. Axis β is orthogonal to the α-axis and the γ-axis.

Figure 6C:
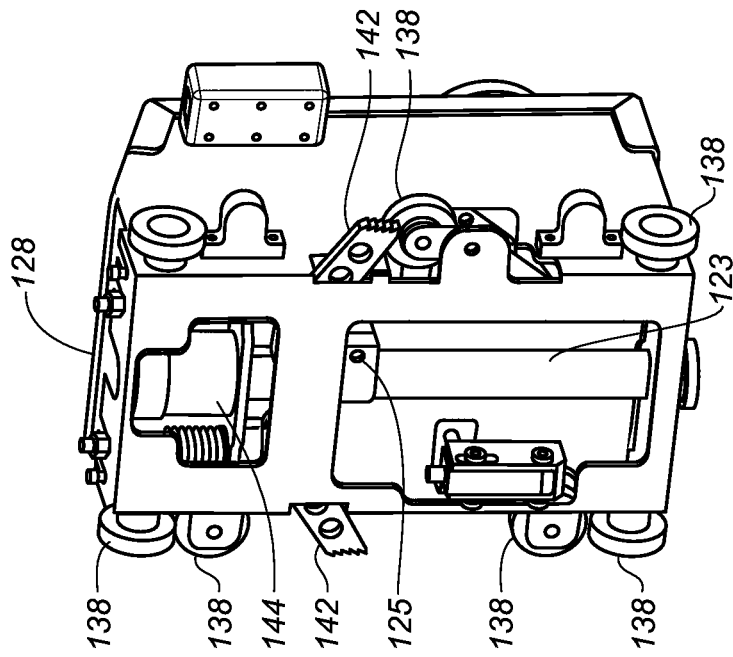
FIG. 6C is a perspective view showing some of the components of a vertical translation apparatus.
Figure 6B:
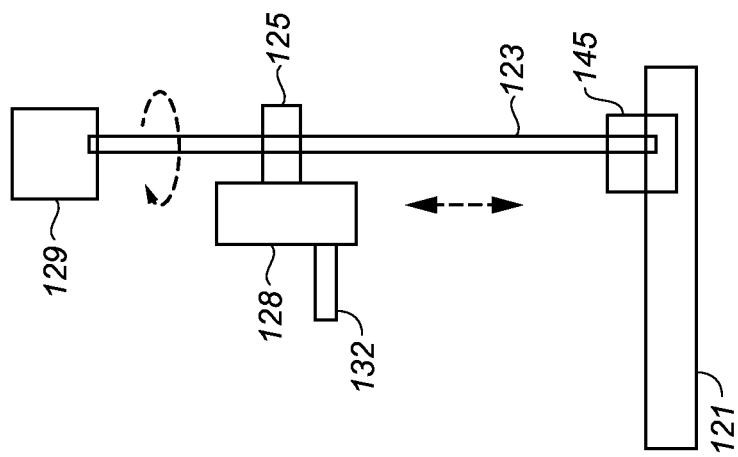
FIG. 6B is a schematic diagram that shows components of the positioning system for the imaging scanner.

It can be appreciated that z-axis translation can be effected in a number of ways. Challenges that must be addressed by the type of system that is used include handling the weight of forked support arm 130 and the imaging scanner 110 that arm 130 supports. This can easily weigh a few hundred pounds. In addition, precautions must be provided for handling conditions such as power loss, contact with the patient, or mechanical problems that hamper positioning movement or operation. According to an embodiment of the application, as shown schematically in FIG. 6B and in the perspective view of FIG. 6C, a vertical actuator 129 rotates a threaded shaft 123. Vertical carriage translation element 128 employs a ball screw mount apparatus 125 to translate rotational motion to the needed linear (e.g., z-direction) motion, thus urging vertical carriage translation element 128 upward or allowing vertical carriage translation element 128 to move downward. Ball screw translation devices are advantaged for handling high weight loads and are typically more efficient than other types of translators using threaded devices. The use of a ball screw arrangement also allows a small motor to drive the shaft that lifts scanner 110 into position and can help to eliminate the need for a complex and bulky counterweight system for allowing control of vertical movement. An encoder 145, such as a linear encoder element, can provide feedback signals that are used to indicate the vertical position of vertical carriage translation element 128.

Vertical carriage translation element 128 travels inside track 112 formed in support column 120 (FIG. 6A); wheels 138 help to guide translation element 128 within the slots. Paired wheels 138 can be orthogonal to each other to provide centering within column 120.

A braking system can also be provided for support column 120. Spring-loaded brakes 142 (FIG. 6C) are positioned to actuate and grip shaft 123 or other mechanical support when mechanical difficulties, power failure, or other conditions are detected. A sensor 144, such as a load cell, is configured to sense rapid movement or interference conditions that are undesirable and to cause brake 142 actuation.

Other features of support column 120 for vertical translation include built-in redundancy, with springs to absorb weight and impact, the load cell to sense a mechanical problem including obstruction by the patient, and manually operable brake mechanisms.

It should be noted that other types of translation apparatus could be used for providing vertical movement of vertical carriage translation element 128. One conventional method for vertical movement control uses a system of pulleys and counterweights to provide lifting force, with motorized assistance. Such an arrangement, however, can be disadvantageous because it can add considerable weight to the column 120 and supporting structure. In spite of its weight-related drawbacks, use of a pulley mechanism can be advantageous for allowing a retractable or telescoping column 120 arrangement, for example, to simplify transport of imaging apparatus 100 between rooms. In one embodiment, the β-axis can be implemented +/−up to 10 degrees. In one embodiment, the horizontal α-axis can be implemented +/−up to 10 degrees. In one embodiment, the γ-axis for a CBCT apparatus can be +/−up to 45 degrees.

Forked support arm 130 can support scanner 110 in a gimbaled arrangement. Source 22 and detector 24 are shown on gantry 36 for reference in FIG. 6A and covered in the alternate view of FIG. 6D. Vertical carriage translation element 128 is configured to ride within a track 112 (FIG. 6A) within support column 120.

For certain exemplary embodiments, some level of manual operability can be provided, such as for power loss situations. In one embodiment, forked support arm 130 can be lifted upwards in position by one or more persons, for example, raising vertical carriage translation element 128 even when brakes 142 are set. Shifting support arm 130 upwards does not release the brakes 142, but simply sets the brakes 142 to hold element 128 position at new levels.

According to an alternate embodiment of the application, vertical carriage translation element 128 can be a motor that moves vertically along supporting threaded shaft 132; alternately, vertical carriage translation element 128 can be driven using a chain, pulley, or other intermediate mechanism that has considerable counterweights for manually raising and lowering vertical carriage translation element 128 and its connected forked support arm 130 and components within support column 120. Additional supporting components include a more complex braking system, such as a pneumatic braking system for providing a force opposing gravity in order to prevent sudden movement of forked support arm 130 as a precaution against damage or injury. Vertical carriage translation element 128 can be automated or may be a manually operated positioning device that uses one or more springs or counterweight devices to allow ease of manual movement of forked support arm 130 into position.

Next, considering the α-axis movement of forked support arm 130, in one embodiment a rotational actuator 136 can be energizable to allow rotation of shaft 132 (FIG. 6A). This rotational actuation can be concurrent with z-axis translation as well as with rotation with respect to the γ-axis.

Figure 6D:
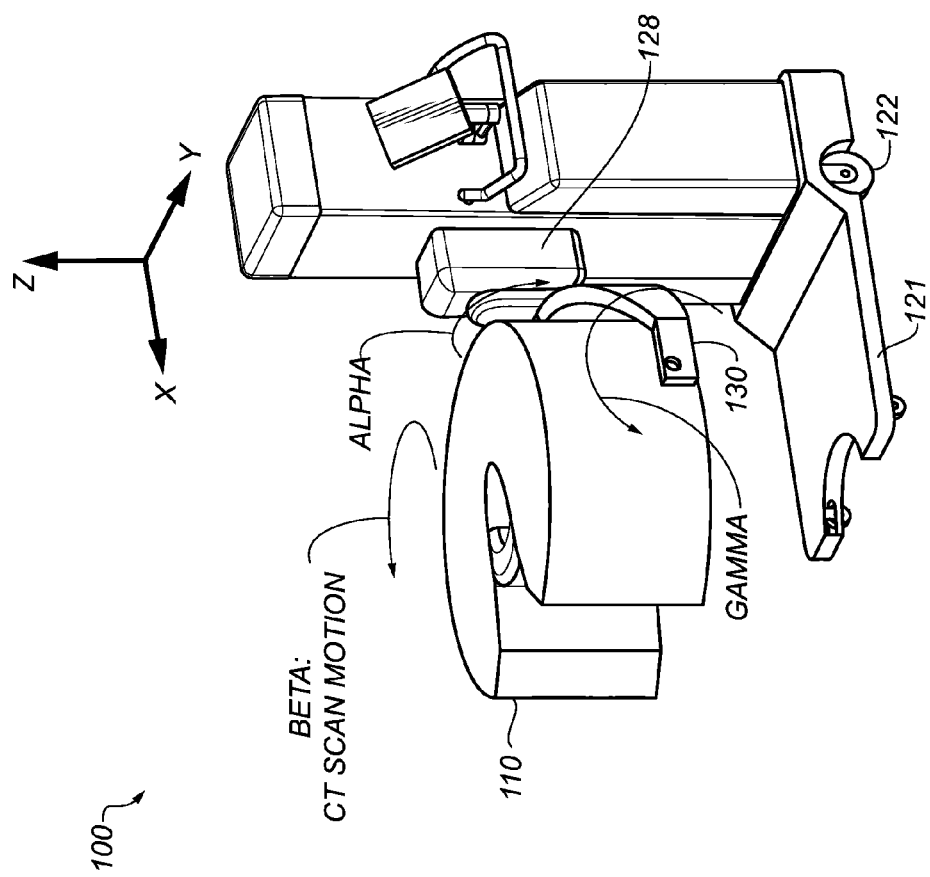
FIG. 6D shows the CBCT imaging apparatus with covers or housing installed.

Forked support arm 130 allows movement relative to the γ-axis according to the position and angle of forked support arm 130. In the example of FIG. 6A, the γ-axis is oriented vertically, substantially in parallel with the z-axis. FIG. 6D shows the γ-axis oriented horizontally. A pivoting mount 140 with a rotational actuator 146, provided by forked support arm 130, allows rotation along the γ-axis. The gimbaled combination of α-axis and γ-axis rotation can allow the imaging apparatus to be set up for imaging in a number of possible positions, with the patient standing, seated, or prone.

Figure 7A:
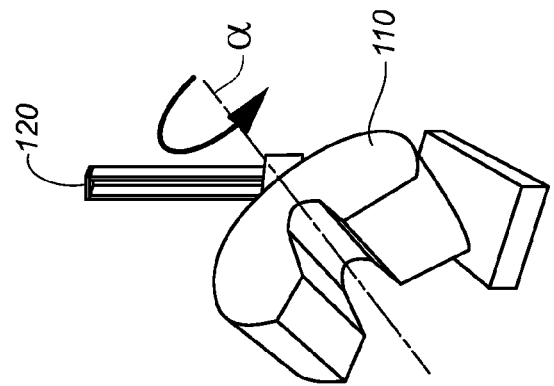
FIG. 7A shows translation of the C-shaped imaging ring, or scanner, with respect to a vertical or z-axis.
Figure 7B:
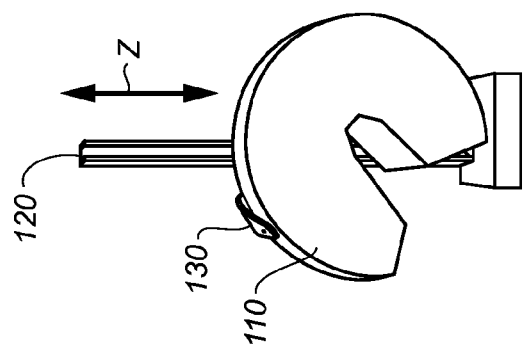
FIG. 7B shows rotation of the C-shaped imaging ring, or scanner, about an $\alpha$-axis that is orthogonal to the z-axis.
Figure 7C:
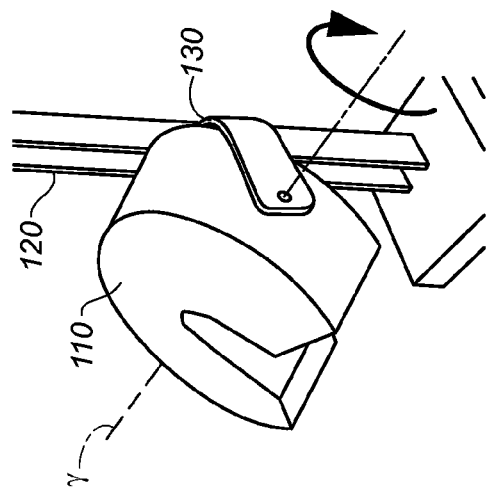
FIG. 7C shows rotation of the C-shaped imaging ring, or scanner, about a $\gamma$-axis that is orthogonal to the $\alpha$-axis.

An exemplary positioning capability of the imaging apparatus 100 is shown n FIGS. 7A-7C. FIG. 7A shows movement of forked support arm 130 on support column 120 to provide z-axis (vertical) translation of scanner 110. FIG. 7B shows rotation of forked support arm 130 about the horizontal α-axis. FIG. 7C shows rotation about the γ-axis as defined by the C-arm arrangement of forked support arm 130.

It should be noted that CBCT imaging apparatus 100 as shown in FIG. 6D provides three degrees of freedom (DOF) for scanner 110 positioning. In addition to the z-axis translation and rotation about α- and γ-axes previously described, casters 122 allow rotation of scanner 110 position with respect to the z-axis as well as translation along the floor.

Referring back to FIG. 5, patient access is provided through an opening, circumferential gap, housing gap, or opening 38 in scanner 110. A door 160, as described herein, is pivoted into place across gap 38 to enclose an inner portion of circumferential gap or opening 38. The door 160 fits between the legs of the patient one extremity of the patient to be imaged is positioned. Once the door (or housing extension) is pivoted into its closed position, it effectively encloses a portion of the detector path that extends outside the housing 78 and protects the curved detector transport 34 path as shown in FIG. 4. With this arrangement, when door 160 is closed to protect the detector transport path, the knee can be examined under weight-bearing or non-weight-bearing conditions. By enclosing the portion of detector transport 34 path that crosses housing gap 38, door 160 enables the extremity to be positioned suitably for 3D imaging and to be maintained in position between the source and detector as these imaging components orbit the extremity in the CBCT image capture sequence. In one embodiment of CBCT imaging apparatus 100, the operator can first enter an instruction at the control console or control panel 124 that specifies the exam type. The system may then automatically adapt the chosen configuration, prior to positioning the patient. Once the patient is in place, manually controlled adjustments to z-axis and α- and γ-axes rotations can be made, as described previously.

FIG. 8 shows a configuration of components of scanner 110 that orbit subject 20 according to an embodiment of the invention. Radiation source 22 and digital radiation detector 24 are mounted in a cantilevered C-shaped gantry 36 that is part of a rotatable transport assembly 170 that can be controllably rotated (e.g., rotatable over an arc about central axis β). Source 22 and detector 24 are thus fixed relative to each other throughout their movement cycle. An actuator 172 is mounted to a frame 174 of assembly 170 and provides a moving hinge for gantry pivoting. Actuator 172 is energizable to move gantry 36 and frame 174 with clockwise (CW) or counterclockwise (CCW) rotation as needed for the scan sequence. C-shaped housing 184 can reduce or keep out dust and debris and/or better protect the operator and patient from contact with moving parts within an interior space of the housing 184.

Figure 9:
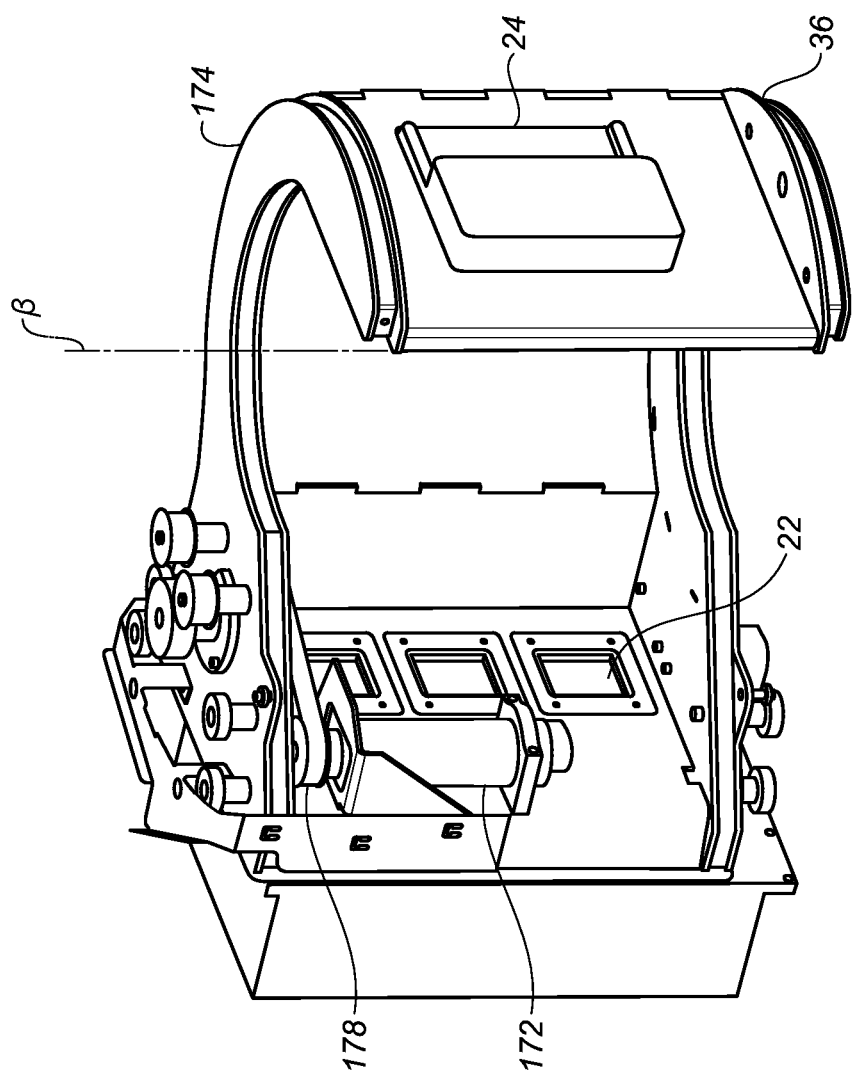
FIG. 9 is a perspective view of a frame that supports scanner components of an extremity imaging apparatus according to an embodiment of the application.
Figure 10:
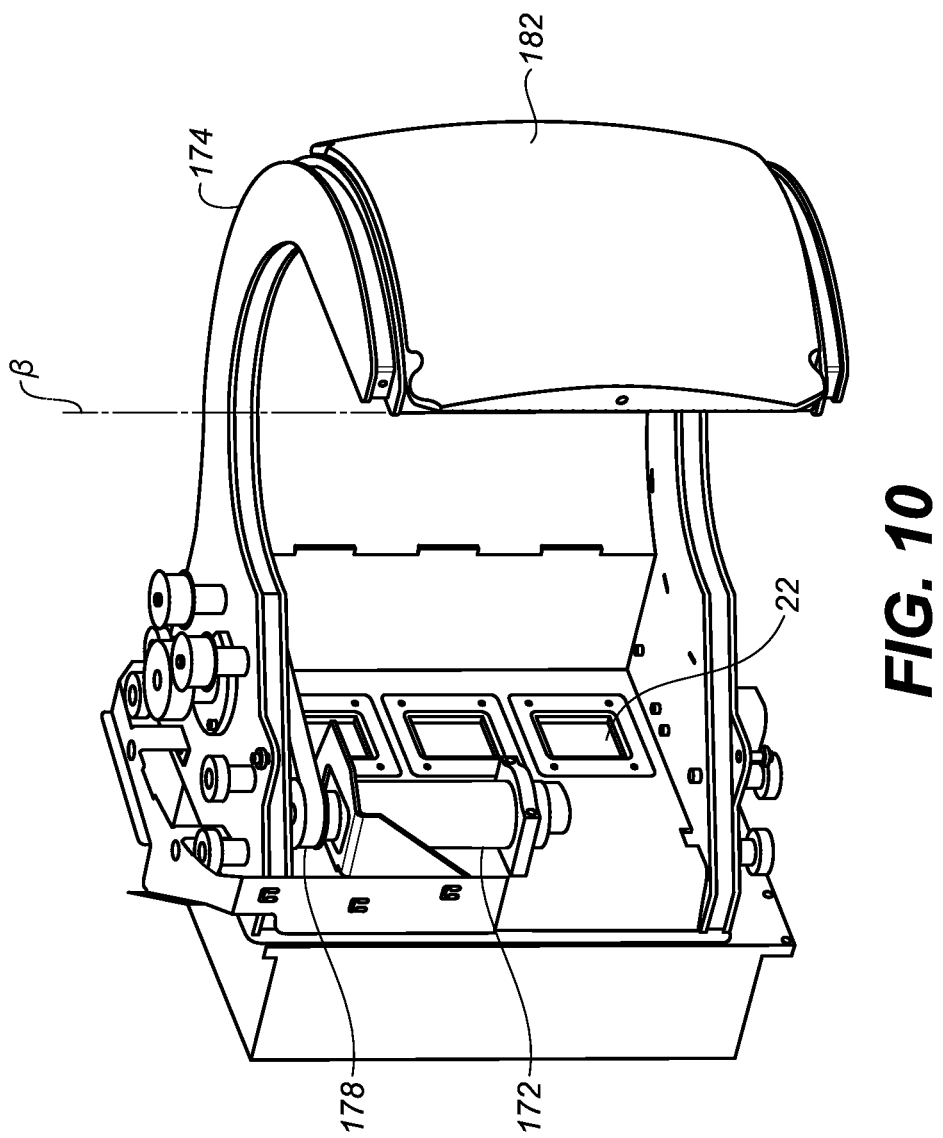
FIG. 10 is a perspective view of a frame that supports scanner components of an extremity imaging apparatus with added counterweight according to an embodiment of the application.

The perspective view of FIG. 9 shows frame 174 and gantry 36 of transport assembly 170 in added detail. Actuator 172 cooperates with a belt 178 to pivot frame 174 for moving source 22 and detector 24 about axis β. The perspective view of FIG. 10 shows frame 174 with added counterweight 182 proximate the detector 24 for improved balance as against the weight of the source 22 of the cantilevered arrangement.

Figure 12:
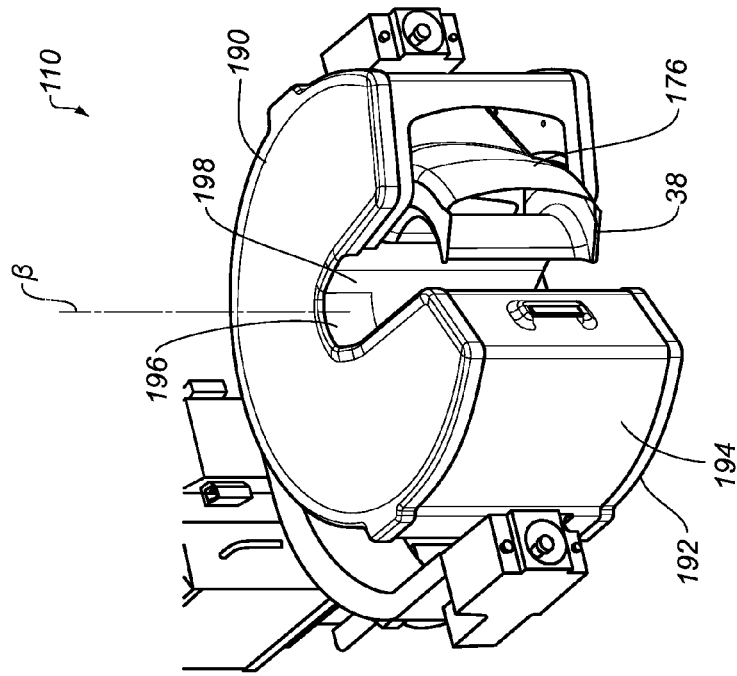
FIG. 12 is a perspective view of the imaging scanner showing a door position between open and closed.
Figure 11:
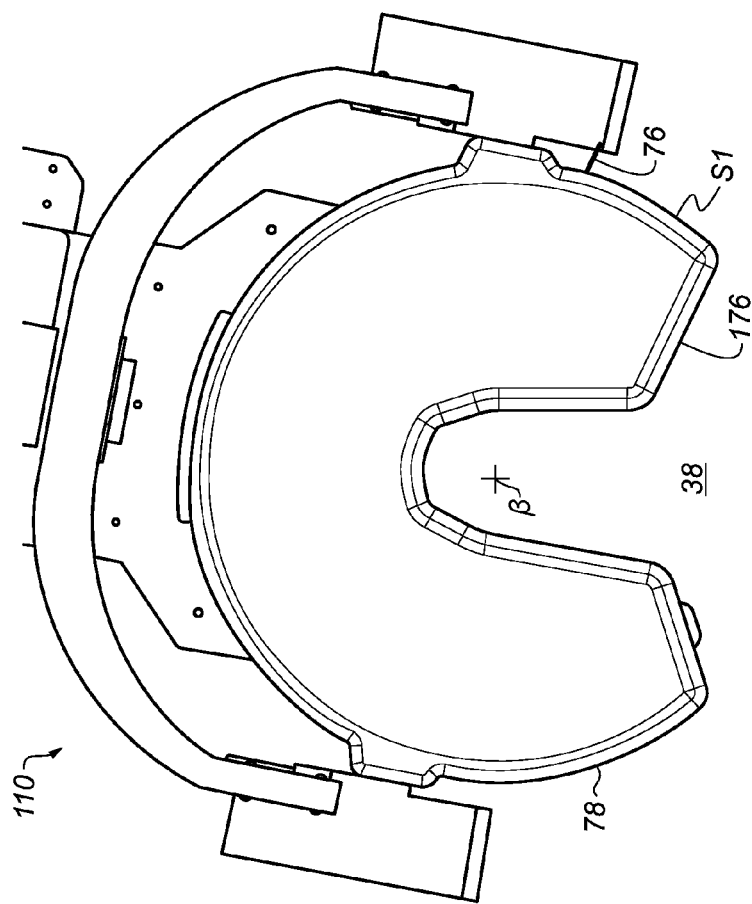
FIG. 11 is a top view of the imaging scanner showing the door, or housing extension, open position with an unobstructed housing gap (or peripheral gap) used for patient positioning at the central axis $\beta$.
Figure 13:
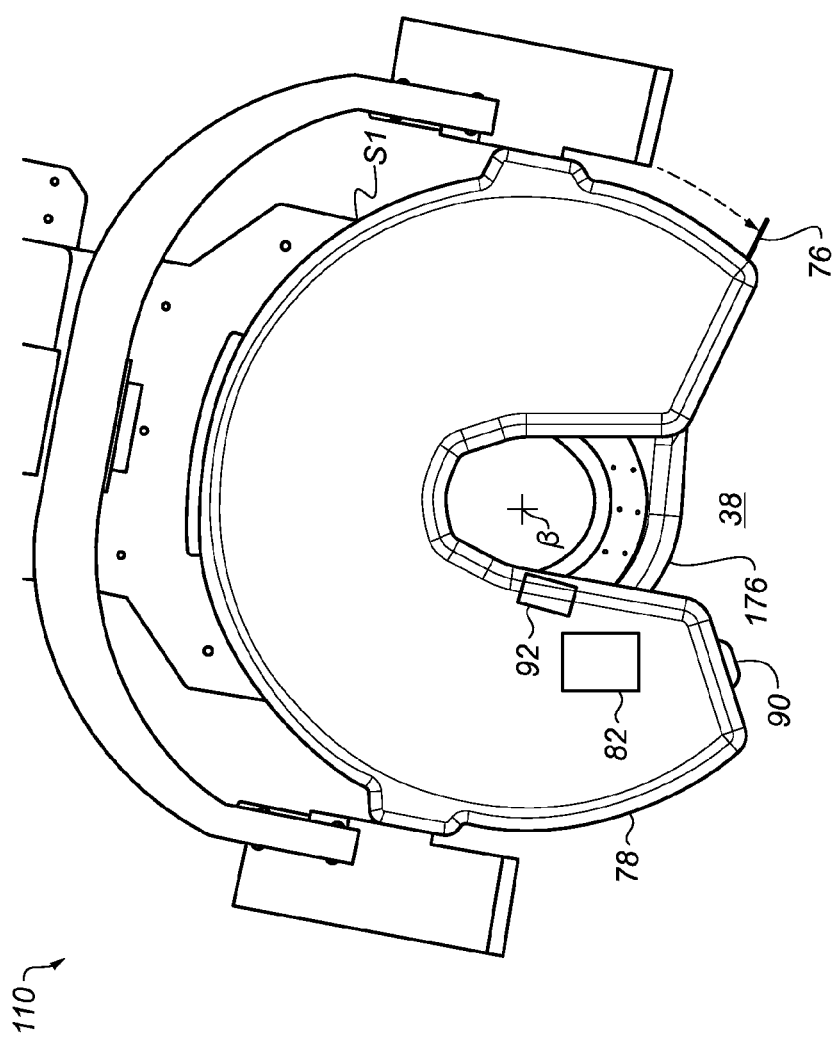
FIG. 13 is a top view of the imaging scanner showing the door, or housing extension, closed position.

Because a portion of the scanning arc that is detector path 28 (FIG. 2) passes across the circumferential gap or opening 38 that allows patient access for positioning at axis (3, this portion of the scan path should be isolated from the patient. FIGS. 11, 12, and 13 show, in successive positions for closing over gap or opening 38, an extendable door, or housing extension, 176 that is stored in a retracted position within scanner housing 180 for providing an enclosure over the detector path 28 once the patient is in proper position. In one embodiment, door 176 can be substantially a hollow structure that, when closed, allows passage of the detector 24 through the structure and around the patient's extremity. Referring to FIG. 9, the portion of frame 174 of gantry 36 that supports detector 24 can pass through the hollow inner chamber provided by door 176 during the imaging scan. At the conclusion of the imaging sequence, frame 174 of gantry 36 rotates back into its home position and door 176 is retracted to its original open position for patient access or egress through the housing gap, or peripheral gap, within housing 180. In one embodiment, the door 176 may be manually opened and closed by the operator. In one embodiment, the door 176 may be opened and closed under motorized control. In one embodiment, interlocks are provided so that movement of scanning transport components (rotation of cantilevered frame 174) is only possible while full closure of the door 176 is sensed.

FIG. 12 also shows top and bottom surfaces 190 and 192, respectively, of scanner housing 180. An outer circumferential surface 194 extends between and connects top and bottom surfaces 190 and 192. An inner radiolucent circumferential surface 196 is configured to connect the top and bottom surfaces 190 and 192 to form a central opening 198 extending from the first surface to the second surface, where the circumferential surface 196 surrounds the β axis.

As shown with respect to FIGS. 2 and 4, in one embodiment radiation source 22 and detector 24 each can orbit the subject along an arc with radii R2 and R1, respectively. According to an alternate embodiment, within source transport 32, a source actuator could be used, cooperating with a separate, complementary detector actuator that is part of detector transport 34. Thus, two independent actuator devices, one in each transport assembly, can be separately controlled and coordinated by an external logic controller to move source 22 and detector 24 along their respective arcs, in unison, about subject 20.

Figure 14:
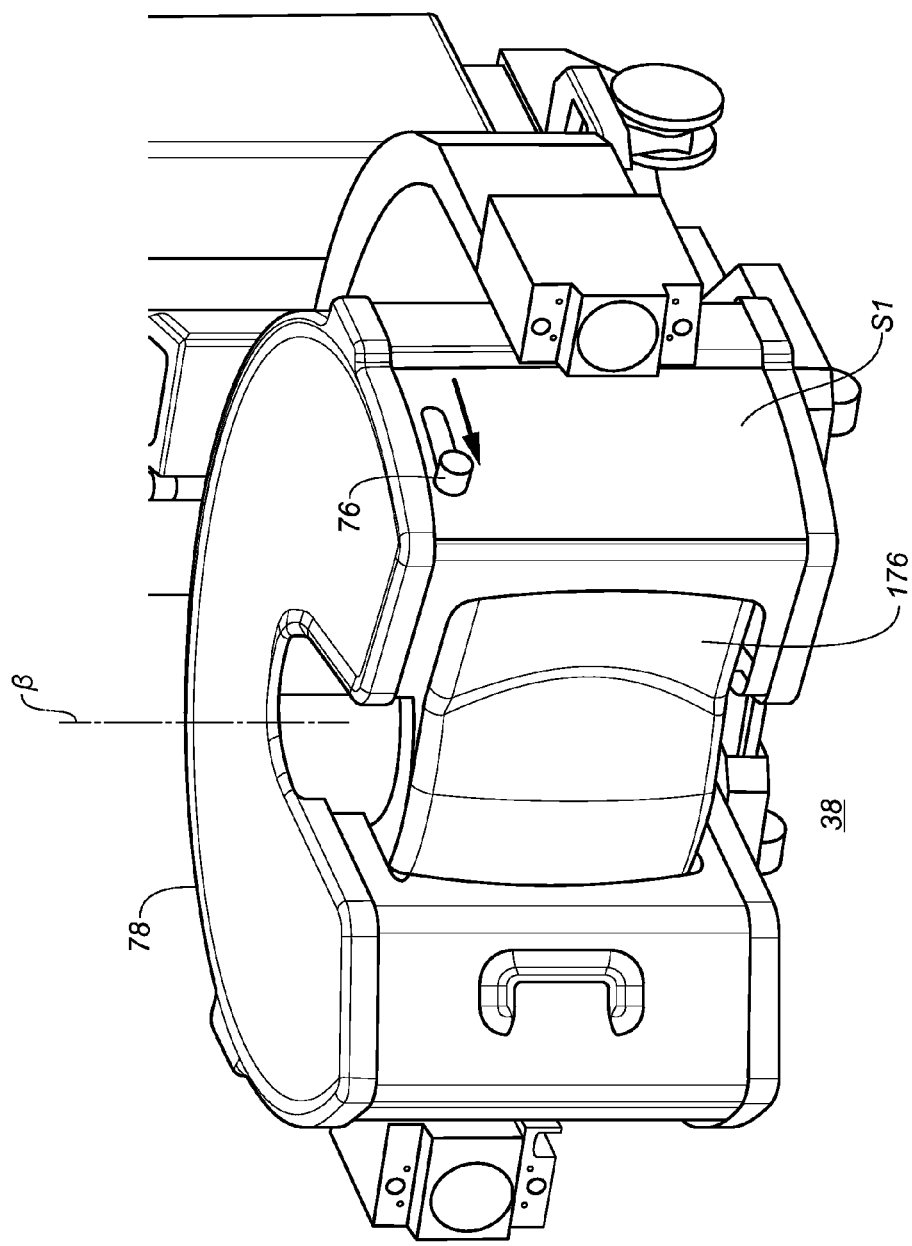
FIG. 14 is a perspective view showing the door in closed position.

FIG. 11 shows scanner 110 with door 176 in open position, not obstructing opening 38, that is, keeping opening 38 clear, allowing patient access for extremity placement within opening 38 at axis β. FIG. 13 is a top view that shows scanner 110 with door 176 in closed position, held by a latch 92. Door 176 thus extends into the opening 38, enclosing opening 38 for imaging of the patient's extremity. A sensor 82 provides an interlock signal that indicates at least whether door 176 is in closed position or in some other position. Movement of internal scanner 110 components such as C-shaped gantry 36 is prevented unless the door 176 is latched shut. A release 90 unlatches door 176 from its latched position. As shown in FIG. 14, handle 76 can be positioned outside of opening 38, such as along surface S1 as shown, for opening or closing door 176. Placement of handle 76 or other type of door closure device, outside of opening 38 is advantageous for patient comfort when closing or opening door 176. As shown in the exemplary embodiment of FIG. 13, handle 76 is operatively coupled with door 176 so that movement of handle 76 in a prescribed direction, such as along the circumference of scanner apparatus 110 housing 78 (e.g., a corresponding direction, or in the clockwise direction shown), causes door 176 corresponding movement (e.g., in the same direction). In one embodiment, clockwise movement of handle 76 causes clockwise movement of door 176, extends door 176 into the opening, and closes door 176; counterclockwise movement of handle 76 causes counterclockwise movement of door 176 and opens door 176, so that it does not obstruct the opening or moves to a position that is clear of the opening.

According to one embodiment, the door 176 is manually pivoted, closed, and opened by the operator. This allows the operator to more carefully support the patient and the extremity that is to be imaged. According to an alternate embodiment, an actuator is provided to close or open the door automatically.

Figure 15:
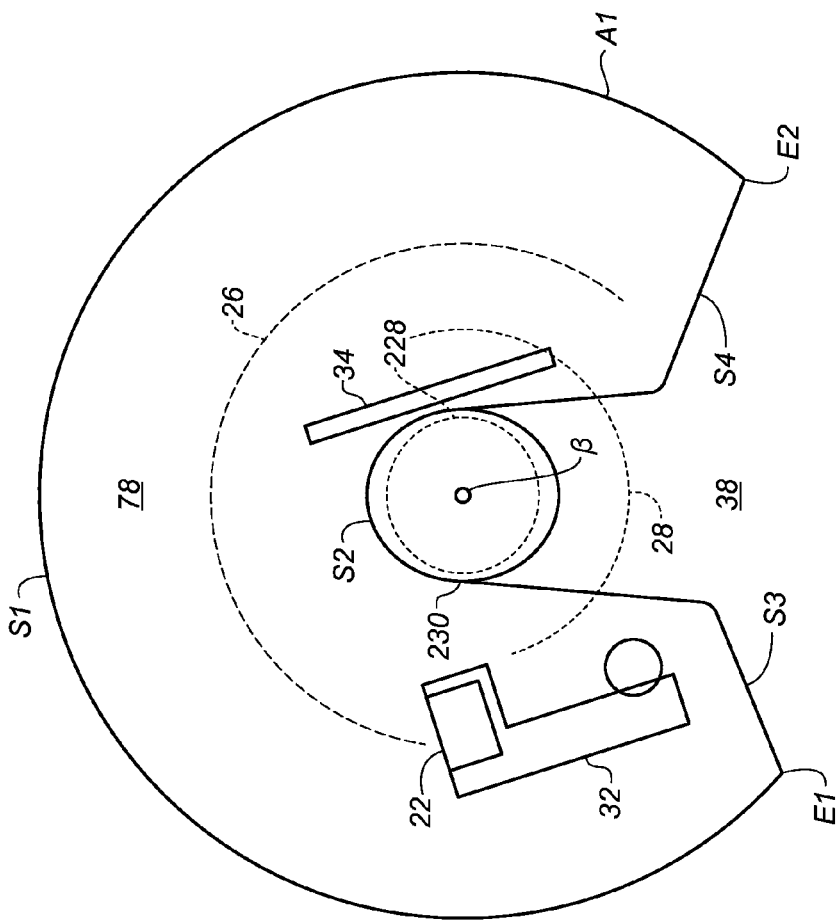
FIG. 15 is a top view of the imaging scanner with a number of its internal imaging components shown, at one end of the imaging scan.
Figure 16:
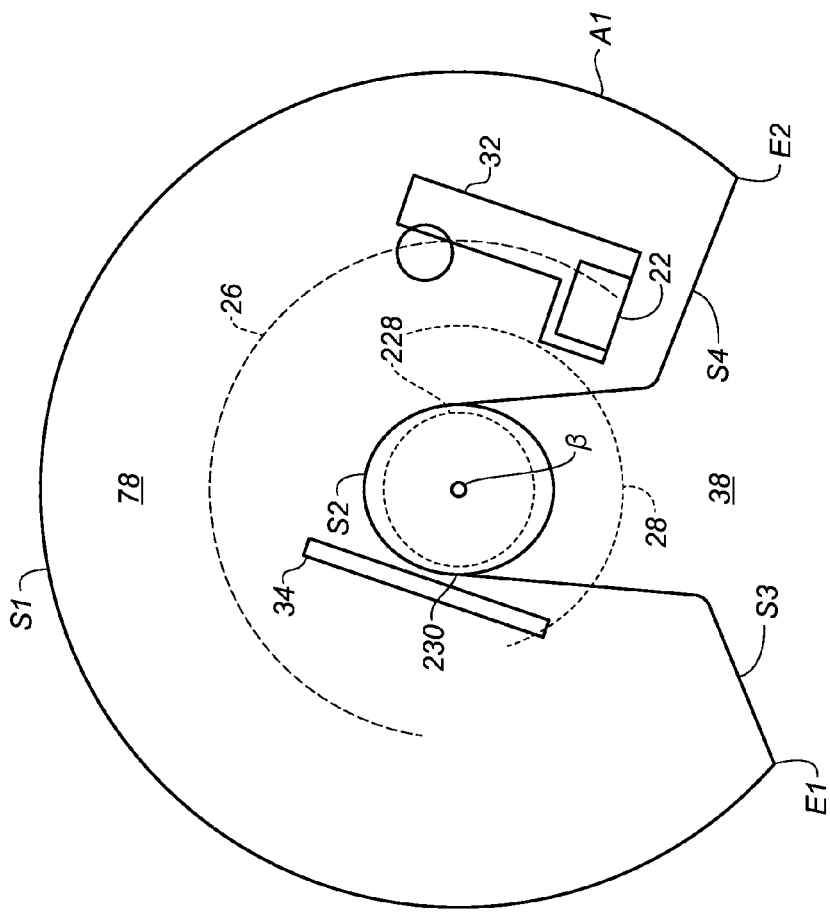
FIG. 16 is a top view of the imaging scanner with a number of its internal imaging components shown, at an opposite end of the imaging scan from that shown in FIG. 15.
Figure 17A:
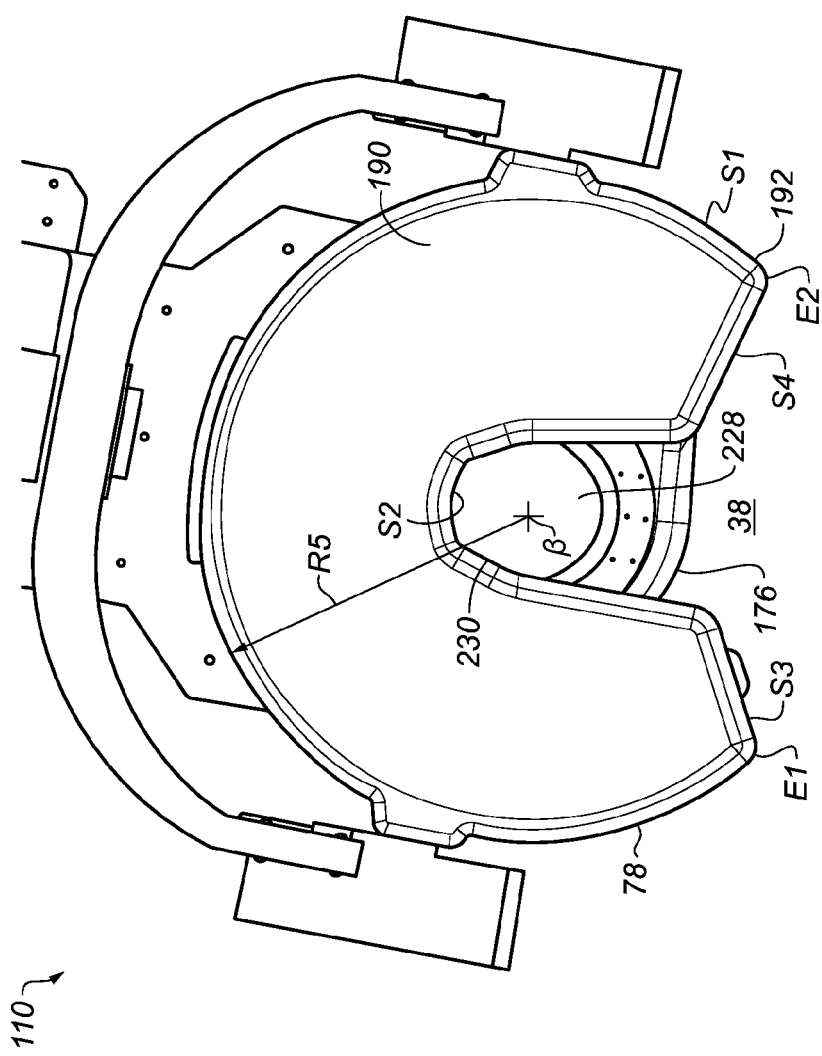
FIG. 17A is a top view of the scanner.

FIGS. 15-16 show a number of features that are of interest for an understanding of how scanner apparatus 110 is configured and operated. FIG. 15 shows how peripheral gap 38 is formed by housing 78, according to an embodiment of the application. Scan volume 228, outlined with a dashed line, is defined by the source and detector paths 26 and 28, as described previously, and typically includes at least a portion of the β axis. An inner central volume 230 can be defined by surface S2 of housing 78 and can typically enclose scan volume 228. Inner central volume 230 can also be defined by door 176 when closed, as shown in FIG. 17A. Peripheral gap 38 is contiguous with inner central volume 230 when door 176 is in open position (e.g., fully or partially opened).

FIG. 15 shows source transport 32 and detector transport 34 at one extreme end of the scan path, which may be at either the beginning or the end of the scan. FIG. 16 shows source transport 32 and detector transport 34 at the other extreme end of the scan path. It should be noted that source 22 is offset along source transport 32. With this asymmetry, the extent of travel of source 22 relative to surface S3 of housing 78 differs from its extent of travel relative to surface S4. At the extreme travel position shown in FIG. 15, source 22 is more than twice the distance from surface S3 as source 22 is from surface S4 at the other extreme travel position shown in FIG. 16. In one embodiment, the inventors may use this distance difference to gain additional clearance for patient positioning with the patient seated.

FIG. 17A shows the configuration of housing 78. In the context of the present disclosure, top surface 190 is considered to be aligned with the top of, at least partially above, or above scan volume 228; bottom surface 192 is aligned with the bottom of, at least partially below, or below scan volume 228. In one embodiment, the top surface 190 or the bottom surface 192 can intersect a portion of the scan volume 228. As shown in FIG. 17A, scan volume 228 can be cylindrical or circularly cylindrical. However, exemplary embodiments of the application are intended to be used with other known 2D scan areas and/or 3D scan volumes. Housing 78 can be metal, fiberglass, plastic, or other suitable material. According to an embodiment, at least portions of top and bottom surfaces 190 and 192 are substantially flat.

As shown in FIGS. 15-17A, the scanner apparatus 110 has a number of surfaces that define its shape and the shape of peripheral gap or opening 38:

(i) an outer connecting surface S1 extends between a portion of top surface 190 and a portion of bottom surface 192 to at least partially encompass the source and detector; at least a portion of the outer connecting surface extends outside the path the source travels while scanning; embodiments of the outer connecting surface S1 shown in FIGS. 15-17A provide an arcuate surface that is generally circular at a radius R5 about center β and that extends, between edges E1 and E2 of the housing;

(ii) an inner connecting surface S2 extends between a portion of the first surface and a portion of the second surface to define an inner central volume 230 that includes a portion of scan volume 228; in the embodiment shown in FIG. 17B, inner connecting surface S2 is approximately at a radius R4 from the β axis. At least portions of inner connecting surface S2 can be cylindrical.

(iii) other connecting surfaces can optionally include a surface S3 that corresponds to a first endpoint of the travel path for source transport 32 (FIGS. 15-16) and is adjacent to curved surface S1 along an edge E1, wherein surface S3 extends inward toward curved inner surface S2; and a surface S4 that corresponds to a second endpoint at the extreme opposite end of the travel path from the first endpoint for source transport 32 and is adjacent to curved surface S1 along an edge E2 wherein surface S4 extends inward toward curved inner surface S2. According to an embodiment, surfaces S3 and S4 are substantially flat and the angle between surfaces S3 and S4 is greater than about 90 degrees. In general, other additional surface segments (e.g., short linear or curved surface segments) may extend between or comprise any of surfaces S1-S4.

Inner and outer connecting surfaces S1, S2, and, optionally, other surfaces, define peripheral housing gap or opening 38 that is contiguous with the inner central volume 230 and extends outward to intersect the outer connecting surface S1 to form gap 38 as an angular recess extending from beyond or toward where the outer connecting surface S1 would, if extended, cross the opening 38. As shown in FIG. 17B, a central angle of a first arc A1 that is defined with a center located within the scan volume and between edges of the peripheral gap 38 determined at a first radial distance R4 outside the scan volume is less than a central angle of a second arc A2 that is defined with the first arc center and between the edges of the peripheral gap 38 at a second radial distance R3 outside the scan volume, where the second radial distance R3 is greater than the first radial distance R4. In one embodiment, as shown in FIG. 17B, a first distance that is defined between edges of the peripheral gap 38 determined at a first radial distance R4 outside the scan volume is less than a second distance between the edges of the peripheral gap 38 at a second radial distance R3 outside the scan volume, where the second radial distance R3 is greater than the first radial distance R4. According to one embodiment, arcs A1 and A2 are centered about the β axis, as shown in FIG. 17B and edges of gap 38 are defined, in part, by surfaces S3 and S4 of housing 78.

The needed room for patient anatomy, such as that described with reference to FIG. 10, can be provided when the central angle for arc A2 is large enough to accommodate the extremity that is to be imaged. According to one embodiment, the central angle for arc A2 between edges of gap 38 exceeds the central angle for arc A1 by at least about 5 degrees; more advantageously, the central angle for arc A2 exceeds the central angle for arc A1 by at least about 10 or 15 degrees.

FIG. 18A is a cross-section view that shows the shape of door 176 in position within housing 78 from a side view. As can clearly be seen in this FIG., door 176 is substantially hollow; its function is to provide a protective shell or covering that isolates the patient from the detector and protects the patient against inadvertent contact with moving parts of the scanning mechanism. With this arrangement, door 176 provides a hollow passage 84 for the detector 24 during an imaging scan. An inner surface 96, facing the inner portions of housing 78, preferably maintains the cylindrical shape of a scan chamber 228 within scanner 110. According to an embodiment of the present invention, hollow passage 84 is substantially tubular.

Figure 18C:
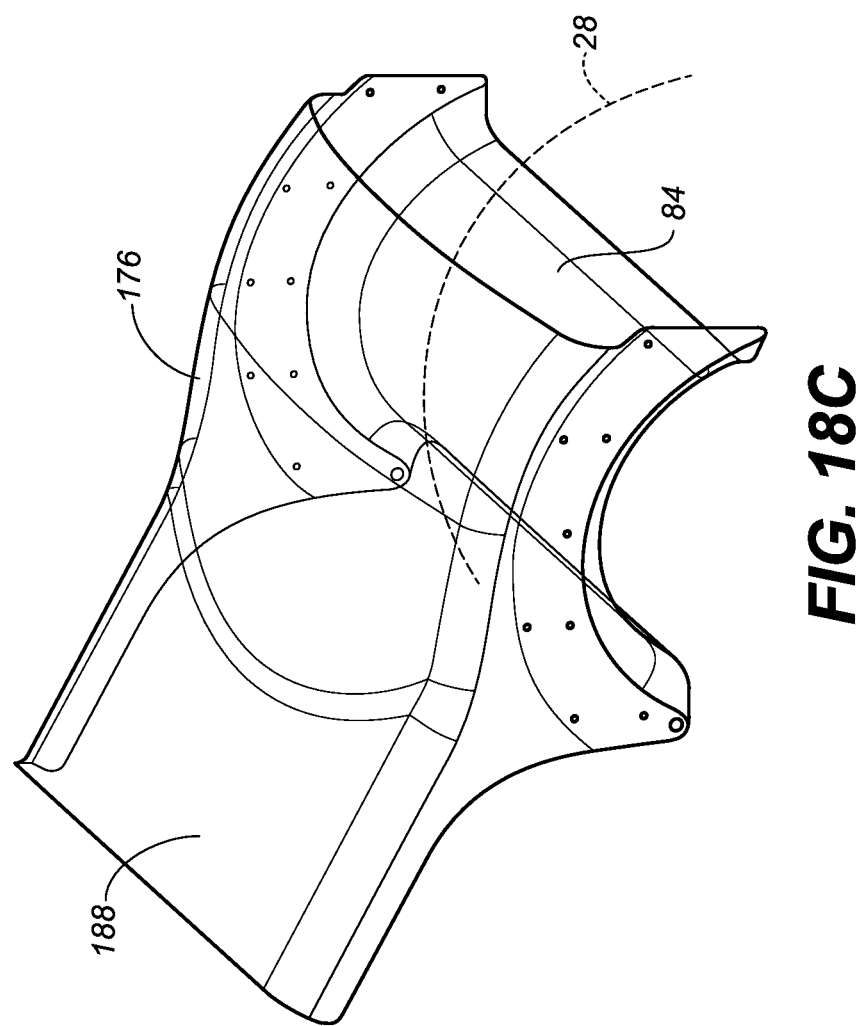
FIG. 18C is an outline view of the door showing the detector path through the hollow passage of the door, or housing extension.
Figure 18D:
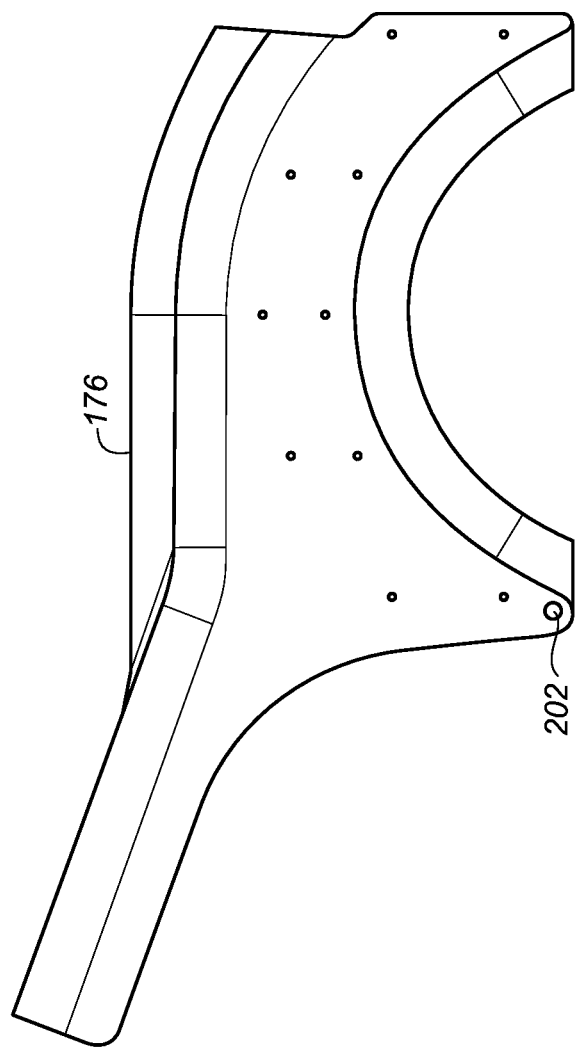
FIG. 18D is a top view of the door, or housing extension.

The design of door 176 has a number of features that help to improve patient comfort and use of extremity CBCT imaging apparatus 100. One feature relates to the cross-sectional shape of door 176, or of at least a portion of door 176 (e.g., an outside surface), as shown in the cross-section view of FIG. 18B. Door 176 is tapered so that it is wider in its middle section and narrows in the direction of central axis β. Thus, door 176 is cross-sectionally barrel-shaped or wedge-shaped. According to another alternate embodiment, a portion of door 176 is notched or otherwise featured to provide a more suitable profile for positioning the patient without obstructing the internal hollow passage 84. In one embodiment, radially outside portions of the door 176 can be narrowed to increase object positioning room and can include an elastic or foam type materials (e.g., without obstructing the detector path). FIG. 18B shows the tapering of the door outline in cross section, where width w2 is reduced from width w1 by at least about 5%. In one embodiment, width w2 is reduced from width w1 by at least about 30-50%. FIG. 18C is a perspective view of the door showing hollow passage 84 with dashed line 28 to indicate the detector path through the door and a closure portion 188, described in more detail subsequently. FIG. 18D is a top view of the door 176, showing a traveling and pivoting point 202 on which door 176 travels and pivots into open or closed position, as described herein. Preferably, the tapering of the door 176 is configured to outside surfaces/shapes to preferably maintain a corresponding shape to the remaining imaging bore yet reduce outer cross-sectional dimensions for patient ease.

FIGS. 19A through 21 show, from a top view, the relative angular rotation of gantry 36 as it pivots about the β axis at different angular intervals in the scan sequence and how the hollow passage 84 provided by door 176 allows a wide angular range of travel for the orbit of detector 24 around the subject being imaged within the scan volume 228. This sequence shows how door 176 covers or surrounds, but does not obstruct, detector path 28 and shows how detector path 28 passes through the hollow interior of door 176 for imaging when the patient is appropriately positioned and door 176 is pivoted into place and latched.

Figure 19A:
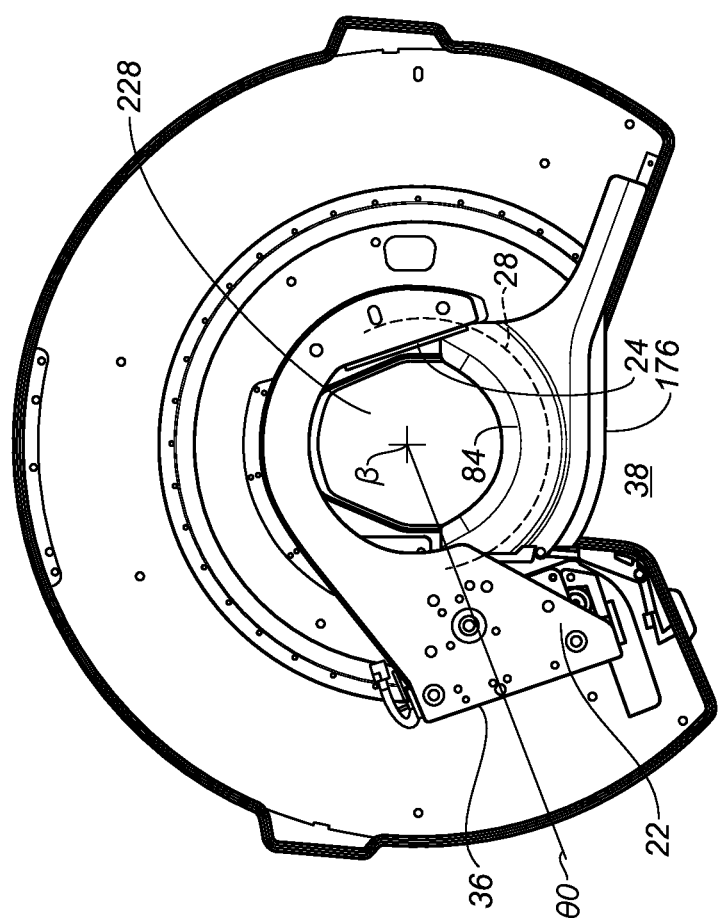
FIGS. 19A, 19B, 20, and 21 are top views that show the sequence of movement of scanning components that is allowable when the door of the scanner is closed.
Figure 19B:
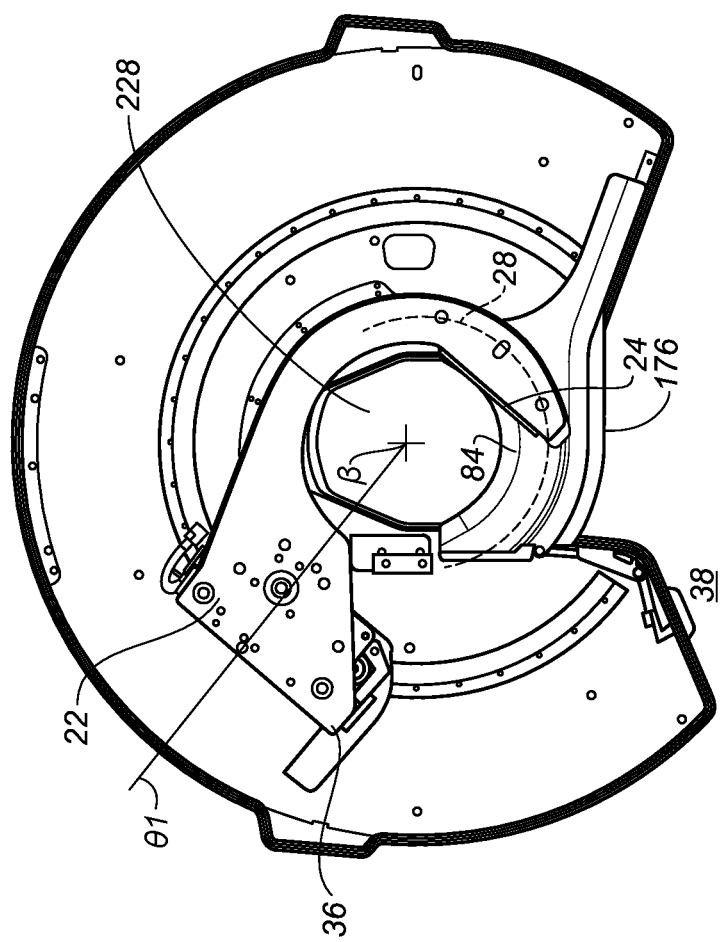
Figure 20:
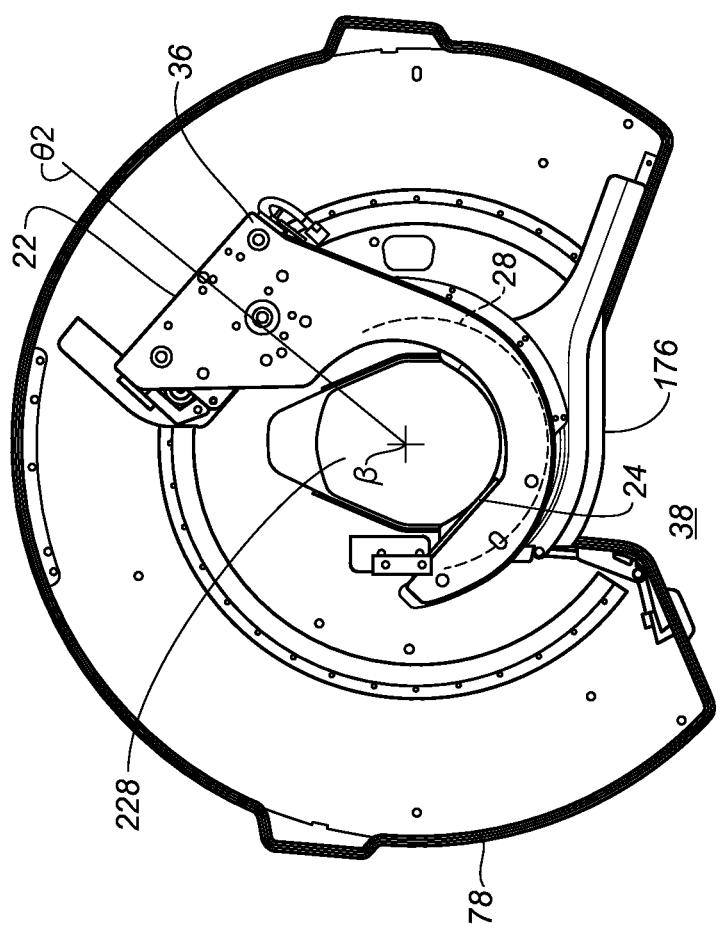
Figure 21:
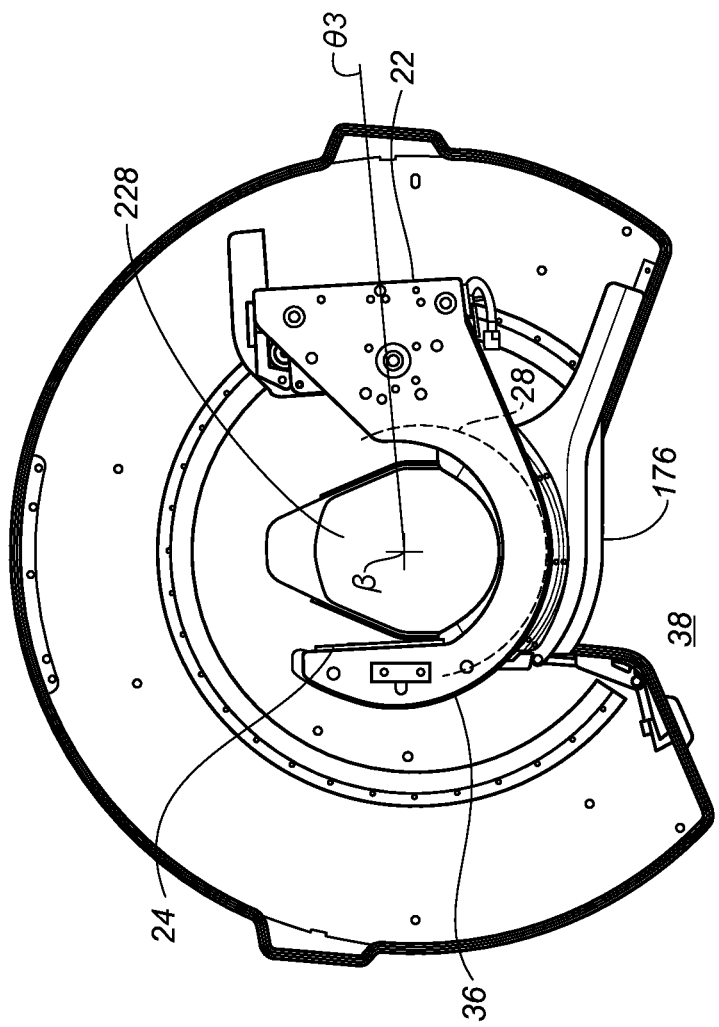

FIG. 19A shows the initial position of gantry 36 at an angle θ0 when door 176 has just been closed. Source 22 and detector 24 are at a rest or default position at angle θ0. Detector path 28 extends into the hollow portion of door 176 as shown. FIG. 19B shows gantry 36 rotated to a second angle θ1 during imaging, at an early portion of the scan. A portion of detector 24 now extends into hollow passage 84 of door 176. FIG. 20 shows gantry 36 rotated to a third angle θ2 as the scan continues. Detector 24 now extends back into housing 78, through door 176. FIG. 21 shows gantry 36 rotated to a fourth angle θ3 near the end of its scan path. Detector 24 now extends past door 176 and into housing 78. Once the imaging sequence is complete, gantry 36 rotates back to its rest position (FIG. 19A) so that door 176 can be opened for patient egress through opening 38.

As the sequence of FIGS. 19A-21 shows, the configuration of door 176 with hollow passage 84 encloses, but does not obstruct, detector path 28 allows C-shaped gantry 36 travel over a considerable range of angles. It should be noted that the full range of angular travel may not be needed for imaging in a particular case. It should also be observed that FIGS. 19A-21 show gantry 36 rotation in a clockwise (CW) direction; rotation of gantry 36 for imaging could alternately be in a counter-clockwise (CCW) direction, proceeding from angle θ3 to angle θ0 according to an alternate embodiment of the present invention.

As noted previously, an interlock arrangement is provided, preventing movement of C-shaped gantry 36 unless the door 176 is fully closed across the opening 38. According to an alternate embodiment, an operator override is provided so that scan operation is permitted from a position with door 176 partially open. According to an alternate embodiment, another feature of door 176 is a closure portion 188 that can cover a door aperture 88 (FIG. 18A) in housing 78 before, during and following door closing.

Figure 22:
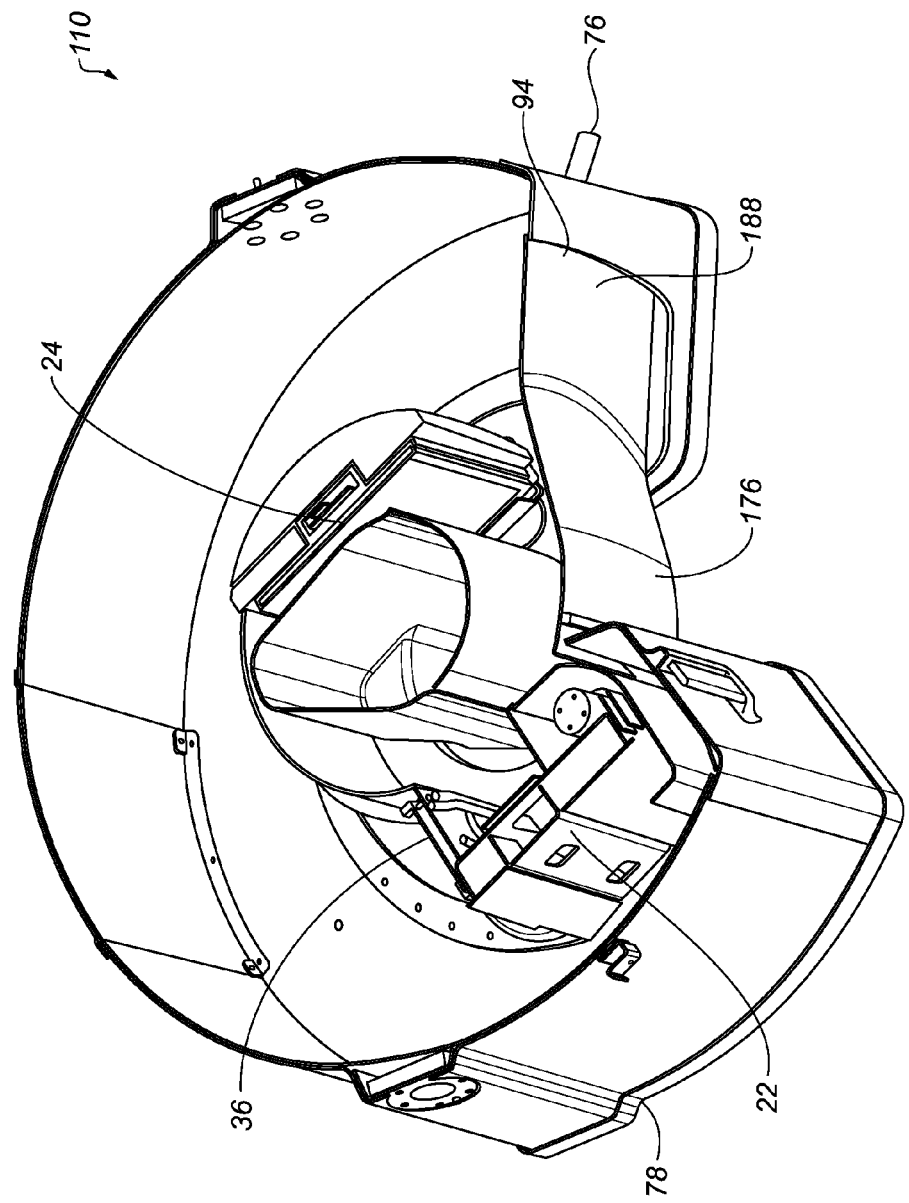
FIG. 22 is a perspective view of the scanner with the housing covers removed, showing the door in closed position.

The perspective view of FIG. 22, with the housing 78 removed for visibility of internal parts, shows another feature of door 176. A closure portion (surface) 188 is provided as a part of door 176 to cover the gap that would otherwise be exposed when the door was closed. This covering keeps out dirt and debris and helps to prevent patient contact with, and visibility of, internal moving parts of scanner 110. According to an alternate embodiment, an edge 94 of closure portion 188 is attached to housing 78 and closure portion 188 folds or bends into place as door 176 pivots toward its closed position.

It is instructive to consider dimensional attributes of the human frame that can be considerations for design of CBCT equipment for scanning extremities. For example, an adult human patient of average height in a comfortable standing position has left and right knees generally anywhere from about 10 to about 35 cm apart. For an adult of average height, exceeding about 35-40 cm (14-15.7 inches) between the knees becomes increasing less comfortable and out of the range of normal standing posture. It is instructive to note that this constraint makes it impractical to use conventional gantry solutions for obtaining the needed 2-D image sequence. For certain exemplary embodiments, either the source or the detector must be able to pass between the legs of a standing patient for knee CBCT imaging, a capability not available with gantry or other conventional solutions.

Figure 23:
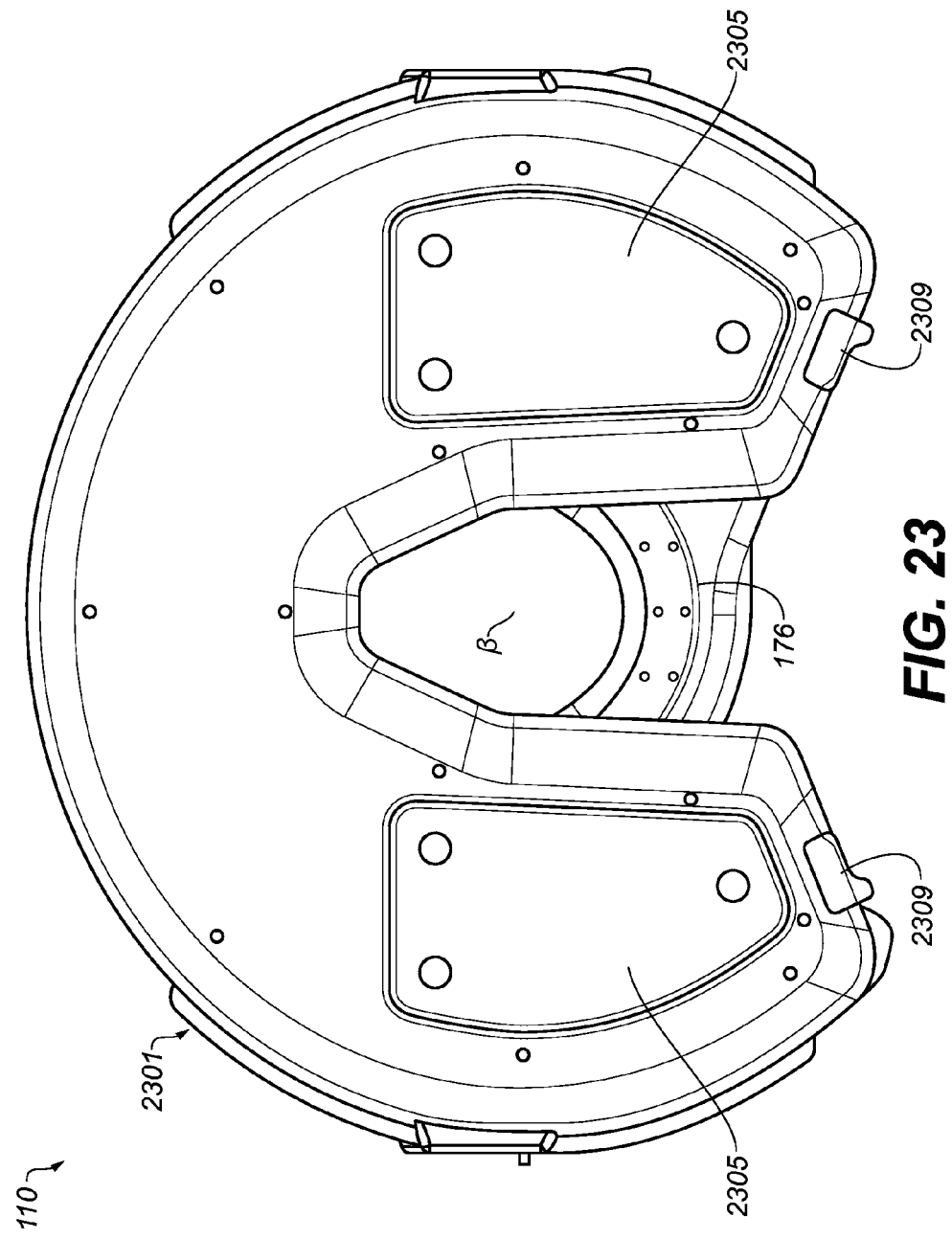
FIG. 23 is a top view of the scanner apparatus and housing extension (door) in a closed position.

FIG. 23 shows another embodiment of the imaging apparatus 110 including an embodiment of a C-shaped housing 176 as previously described herein. The C-shaped housing 176 generally surrounds the central axis β of the detector and source paths, which are enclosed by the C-shaped housing 176. The exterior upper surface of the C-shaped housing includes two symmetrical indentations 2305 for placement of cushions or pads. The housing extension (door) 176 is shown deployed from one end of the housing 176 across the housing gap 38 to a closed position. In the closed position, the housing extension 176 encloses the detector 24 as it travels across the housing gap during a scan of a patient extremity, which may be placed at or proximate the central axis β within the depth of the C-shaped housing 176. Manual latch controls 2309 may be used to secure the housing extension 176 in open and closed positions. In one embodiment, the latch controls 2309 may be biased to automatically secure the housing extension 176 in an open or closed position when the housing extension 176 is fully retracted or fully deployed, respectively. The latch controls 2309 may then be manually released to allow the housing extension 176 to be moved.

Figure 24:
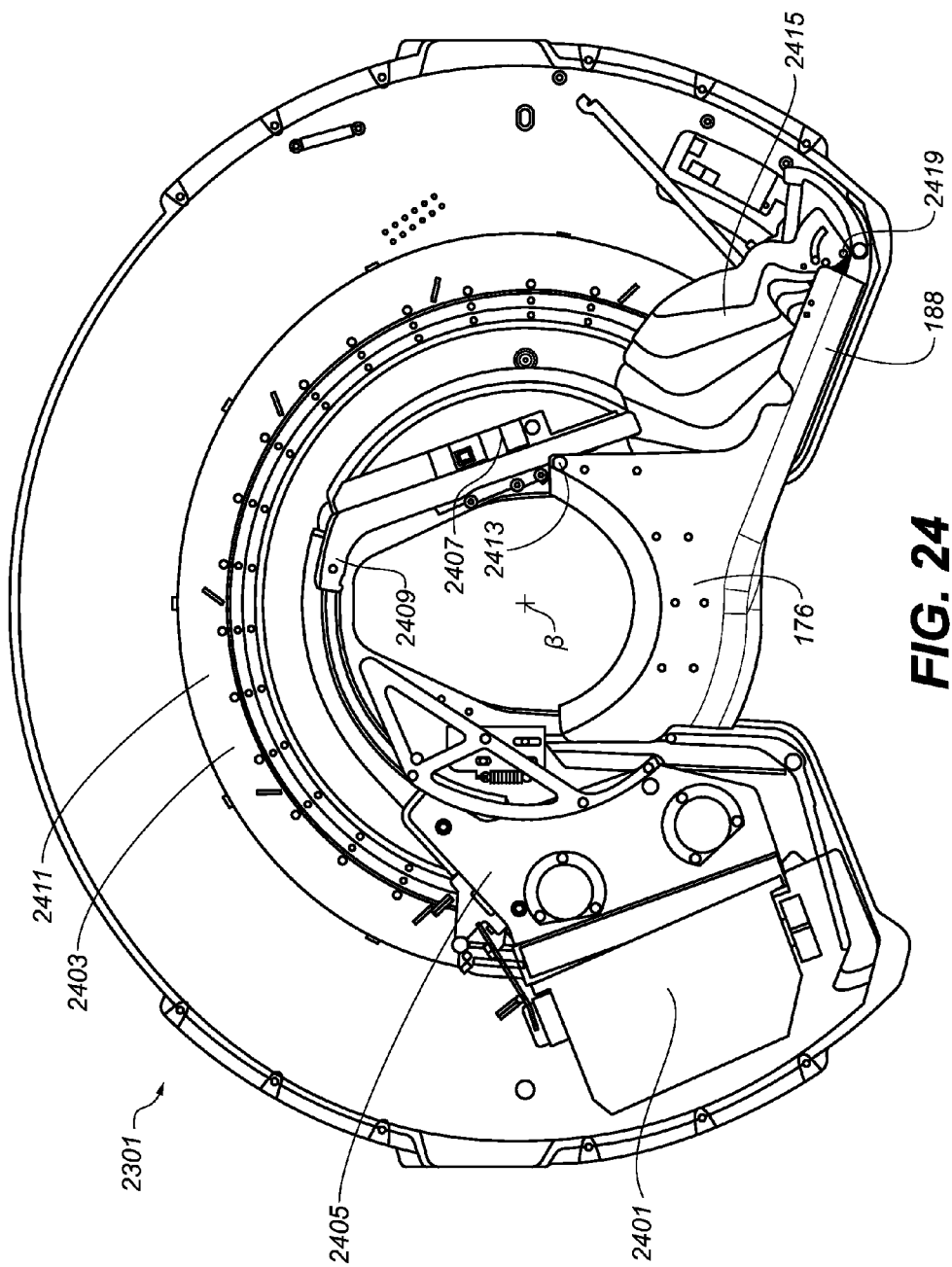
FIG. 24 is a partial transparent diagram of the scanner apparatus of FIG. 23 with the housing extension (door) in a closed position.

FIG. 24 is a schematic view of an interior of the C-shaped housing 176 of the imaging apparatus 110. The x-ray source 22 is fixed within source assembly 2401 which, in turn, is secured to turntable 2403 by a rigid source assembly arm 2405. The detector assembly 2407 includes the detector 24 secured in a position diametrically opposite from the source assembly 2401 in relation to the central axis β. Similar to the source assembly 2401, the detector assembly 2407 is secured to turntable 2403 by a rigid detector assembly arm 2409. To capture radiographic images of a subject in the detector 24, the source assembly 2401 and the detector assembly 2407 travel along the turntable track 2411 as they are revolved about a subject to be imaged positioned at central imaging axis β. The source 24 is activated to emit radiographic radiation that travels through the subject and is captured by imaging pixels in the detector 24. The rigid hollow housing extension (door) 176 is shown fully deployed (extended) from one end of the C-shaped housing 176 across the housing gap 38 to a closed position. In this closed position, the detector assembly 2407 may travel through the inside of the housing extension 176 as the source and detector assemblies revolve within the C-shaped housing (FIGS. 19A-21) during an x-ray scan. Thus, the detector assembly 2407 and its rigid detector assembly arm 2409 remain enclosed at all times by the C-shaped housing and/or the housing extension 176 during a patient scan.

Movement of the housing extension 176 across the housing gap 38 to opened and closed positions involves pivoting the housing extension 176 about a traveling pivot axis 2413 that is also part of a hinge assembly (FIGS. 30A-F). Thus, the housing extension 176 travels and pivots, as it is opened and closed, together with its traveling and pivoting hinge, as described hereinbelow. The portion of the housing extension 176 that corresponds to, and coincides with, the traveling pivot axis 2413 is shown in FIG. 18D as traveling and pivot point 202. Also visible in FIG. 24 is a fanned blade assembly 2415 for shielding an interior space of the housing against exterior access and/or visibility. The fanned blade assembly rotates about a fan hinge pin 2419. A portion 188 of the housing extension 176 also serves to shield an interior space of the housing 176 against exterior access and/or visibility through opening 88 (FIG. 18A) when the housing extension 176 is closed as shown.

Figure 25:
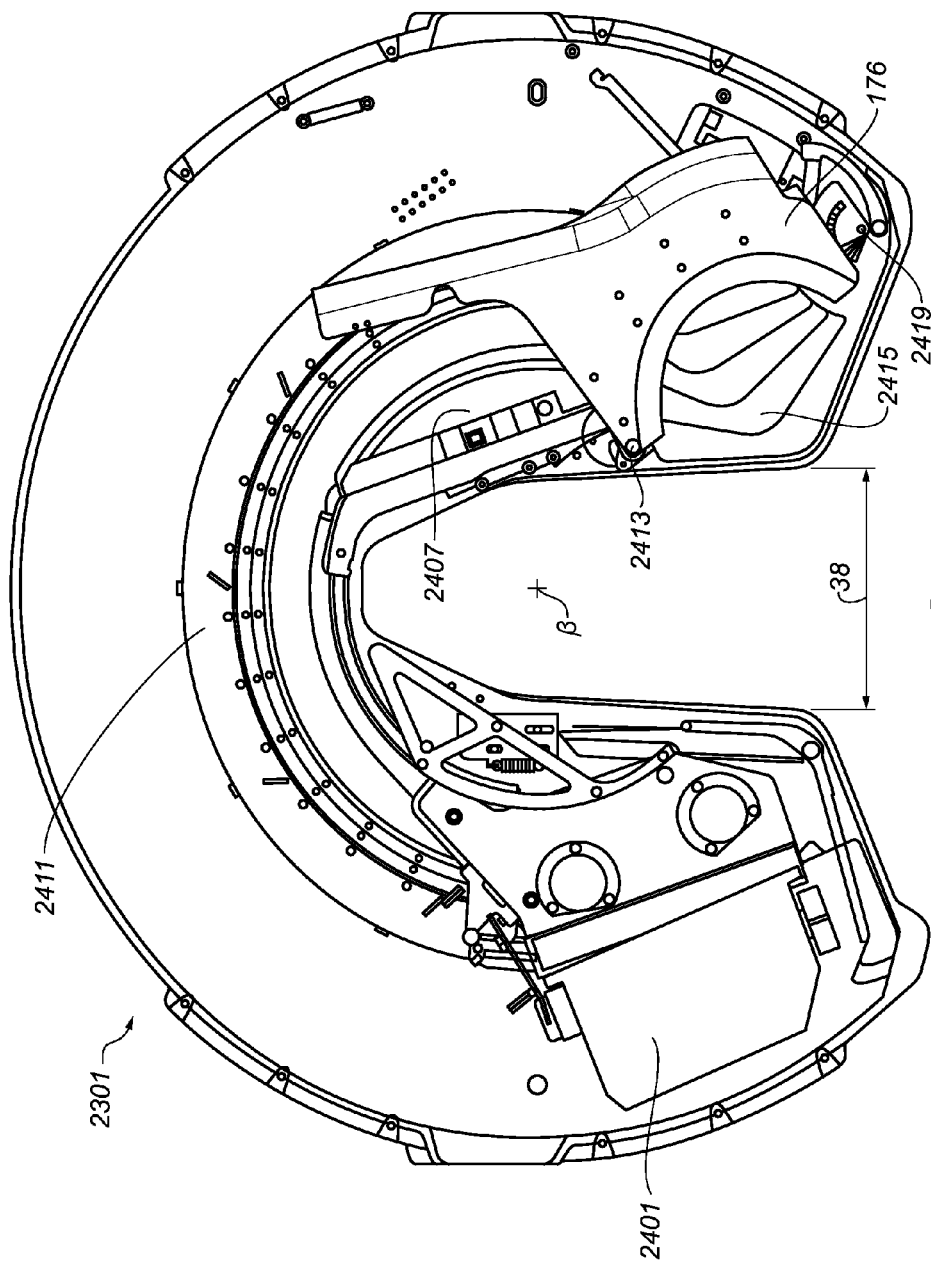
FIG. 25 is a partial transparent diagram of the scanner apparatus of FIG. 23 with the door in an opened position.

FIG. 25 illustrates one embodiment wherein the housing extension 176 is fully retracted to an open position entirely within the housing 2301. The retraction, or opening, of the housing extension 176 into the housing 2301 occurs as the housing extension 176 travels and pivots about traveling pivot axis 2413, in a counterclockwise direction as shown in the view of FIG. 25. In this position, the housing gap 38 is fully open and accessible to allow an extremity of a patient to be positioned at or near the central axis β by moving the extremity through the housing gap 38. After positioning of the patient extremity, the housing extension 176 may be deployed or closed around the patient extremity in order to begin an x-ray scanning procedure by revolving the source assembly 2401 and the detector assembly 2407 about central axis β along the turntable track 2411.

Figure 26:
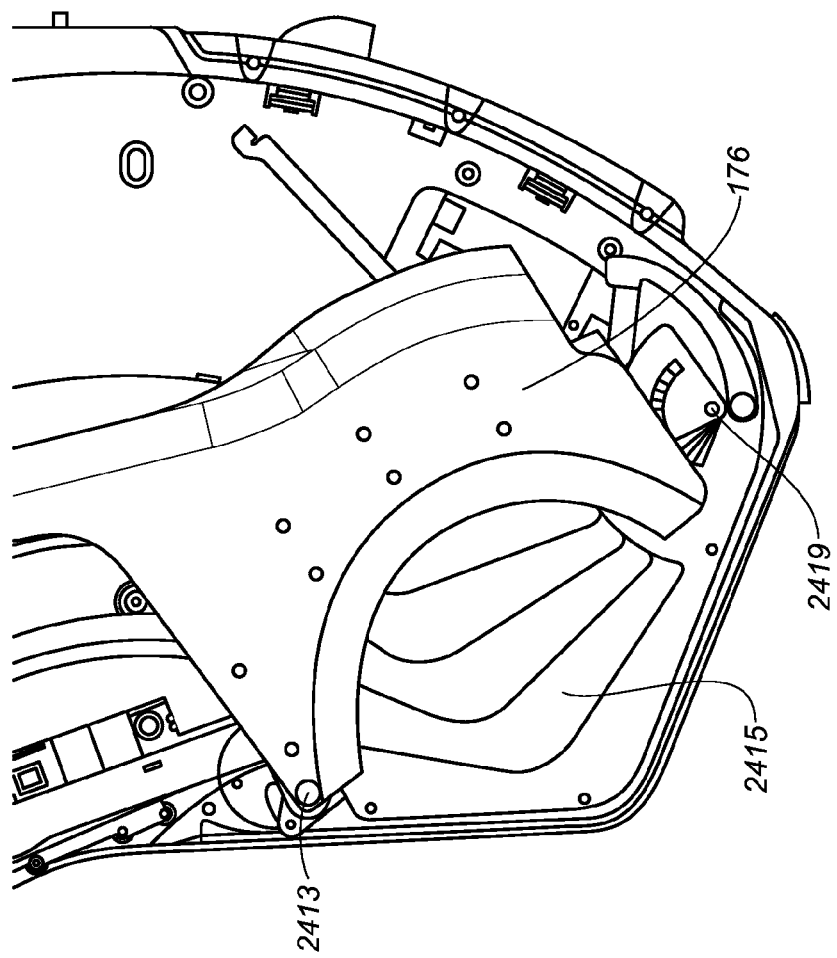
FIG. 26 is a cross-section diagram of a portion of the scanner apparatus at the door attachment area with the housing extension open.

FIG. 26 illustrates a close up schematic view of one end of the C-shaped housing wherein the housing extension 176 retracts when fully opened, as shown. The fanned blade assembly 2415 is spread in this position to shield a portion of the interior of the C-shaped housing 2301 from exterior access. The fanned blade assembly 2415 may be mechanically biased to either an opened or closed position, however, the fully opened position of the housing extension 176 interacts with the fanned blade assembly 2415 to mechanically spread the individual blades which are all attached to a portion of the housing 2301 at a pivot point 2419.

FIG. 27 illustrates a latch assembly 2701 in position to secure the housing extension 176 in a open position and to shield an interior space of the housing from exterior access and/or visibility when the housing extension 176 is fully opened. Latch assembly 2701 may be manually released using latch control 2309, such as when the housing extension 176 is to be moved to a closed position.

FIG. 28 illustrates a housing shield, or door, 2801 that is placed in position over opening 2803 to shield an interior space of the housing 2301 from exterior access and/or visibility when the housing extension 176 is opened. The shield 2801 is mechanically biased to automatically close when the housing extension 176 is retracted from a fully closed position, and to automatically open when the housing extension 176 is fully closed. The opening 2803 receives one end of the housing extension 176 when the housing extension 176 is fully deployed (closed). When fully deployed, edges of the housing extension 176 contact matching edges of the opening 2803 to enclose the detector assembly 2407 as it travels out of one end of the C-shaped housing 2301 across the housing gap 38 and through the opening 2803 into the other end of the C-shaped housing (FIGS. 19A-21) during an x-ray scanning procedure.

Figure 29A:
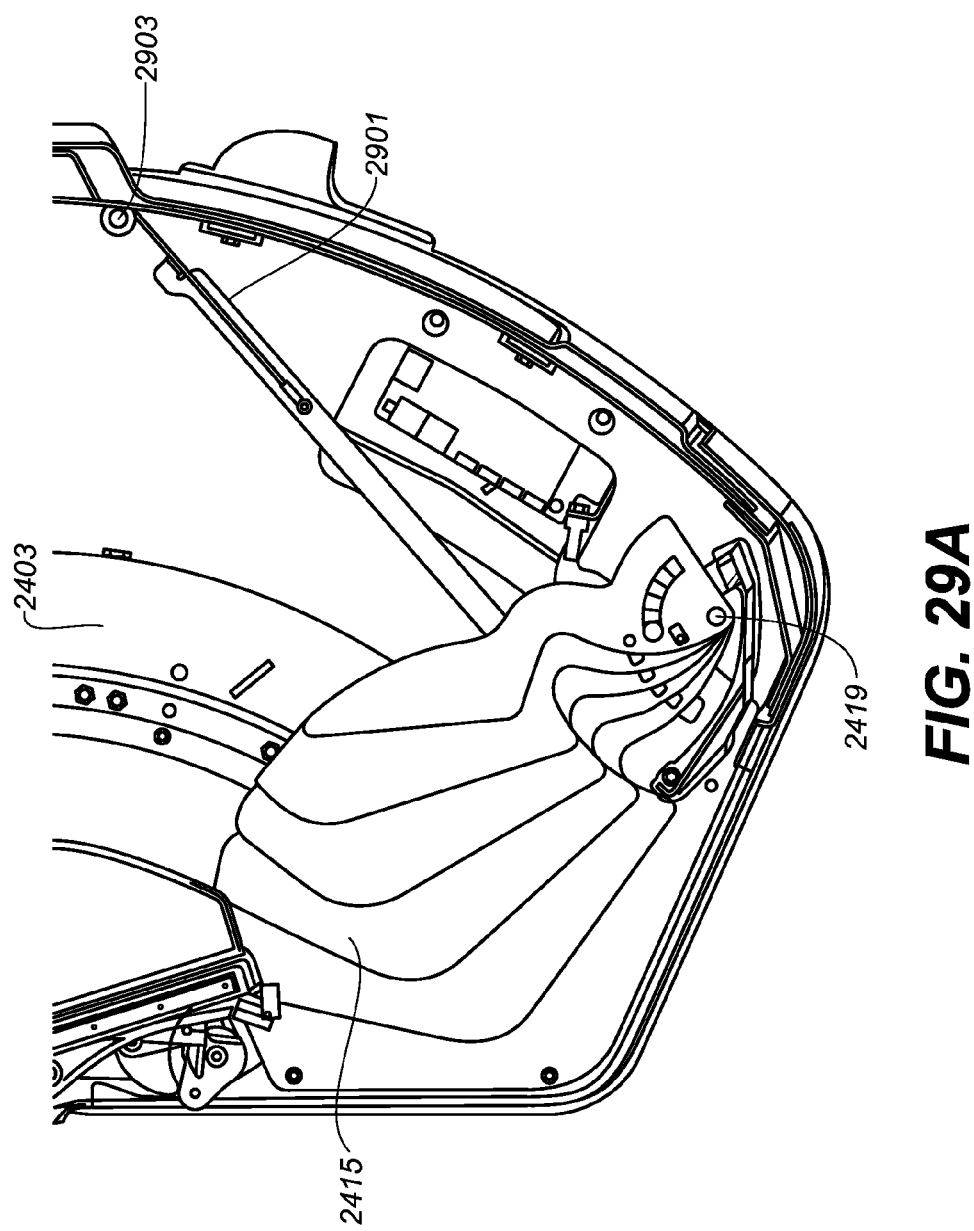
FIG. 29A is a cross-section diagram of a portion of the scanner apparatus at the door attachment area.

FIG. 29A illustrates a close up schematic view of one end of the C-shaped housing 2301 wherein the housing extension 176 retracts when fully opened, but with the housing extension 176 removed from view. A blade retraction arm 2901 is attached at one end to a loop 2903 formed in an interior wall of the housing 176 and is attached at another end to fanned blade assembly 2415. In one embodiment, the blade retraction arm 2901 may be spring biased to open (spread) the blade assembly 2415. The housing extension 176 may be configured so that it mechanically closes the fanned blade assembly 2415 (FIG. 29B) by direct contact with the fanned blade assembly 2415 or with the blade retraction arm 2901, when the housing extension 176 is moved to a closed position.

FIG. 29B illustrates a close up schematic view of one end of the C-shaped housing 2301 wherein a portion of the housing extension 176 is shown extended from one end of the housing 2301 across housing gap 38 to a closed position. The fanned blade assembly 2415 is closed (compressed) when the housing extension 176 is closed and source assembly 2401 approaches one end of the source path. In one embodiment, the housing extension 176 does not mechanically interact with the fanned blade assembly 2415, however, the source assembly 2401 may instead be configured to close the fanned blade assembly 2415 by direct contact with the fanned blade assembly 2415 or with the blade retraction arm 2901, when the source assembly 2401 approaches one end of the source path, as shown.

Figure 30D:
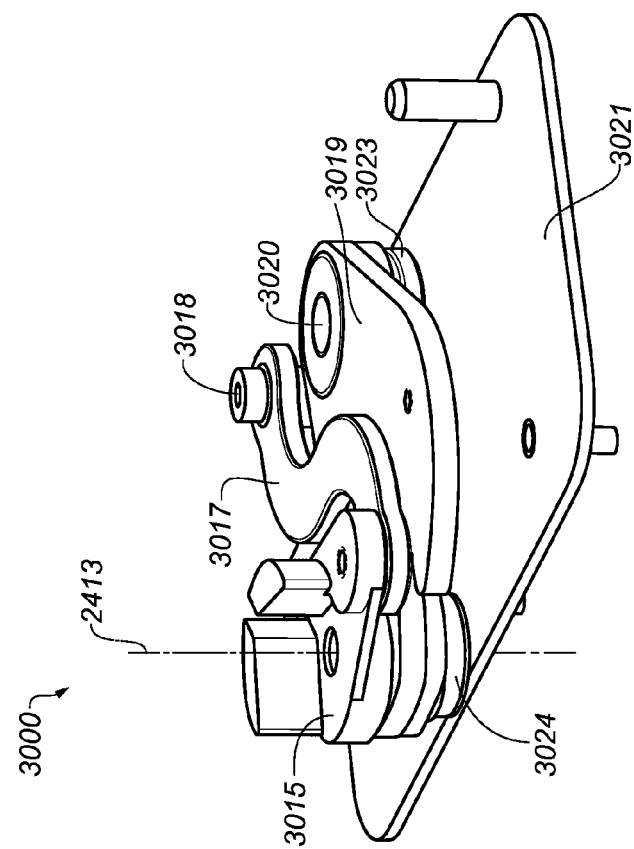
FIGS. 30C-30D are diagrams that show the embodiment of the hinge mechanism of FIGS. 30A-30B where the housing extension is between an open and a closed position.

FIGS. 30A-F illustrate a hinge assembly 3000 that provides the traveling pivoting movement for the housing extension 176 described herein. FIGS. 30A, C, E illustrate a top view of the hinge assembly 3000 and are paired with the corresponding perspective view of FIGS. 30B, D, F, respectively. Hinge assembly 3000 establishes a traveling pivot (rotating) axis 2413 that simultaneously moves and rotates the housing extension 176 into open/closed positions. The hinge assembly 3000 as shown is attached to the housing extension 176 at a top side of the housing extension 176. A complementary paired hinge assembly is also attached to a bottom side of the housing extension 176 to provide stable support and the traveling pivoting movement to open and close the housing extension 176 as described herein. The hinge assembly 3000 includes four main components: a traveling and pivoting door support 3015, an S-link 3017, a hinge plate 3019, and a base plate 3021. These components may be made from steel, aluminum, or other suitably rigid and resilient materials. The moving components travel in planes parallel to one another and parallel to the plane of the (stationary) base plate 3021. The rotational axes of these components are substantially perpendicular to the movement planes and the plane of the base plate 3021. Other parts of the hinge assembly 3000 shown in the Figures and not described in detail herein may include washers, spacers, means for securing in position the pins at the rotating axes, alignment pins, attachment pins for attaching the hinge assembly to the housing, and stop posts, for example.

As shown in FIGS. 30A-F, the base plate 3021 remains stationary while the other main components travel or rotate in relation thereto. The base plate 3021 is fixedly attached to an interior structure of the housing 2301, while the housing extension 176 is attached to the traveling and pivoting door support 3015 such that the traveling pivoting point 202 (FIG. 18D) of the housing extension 176 is aligned with the traveling pivot axis 2413 of the traveling and pivoting door support 3015.

Figure 30C:
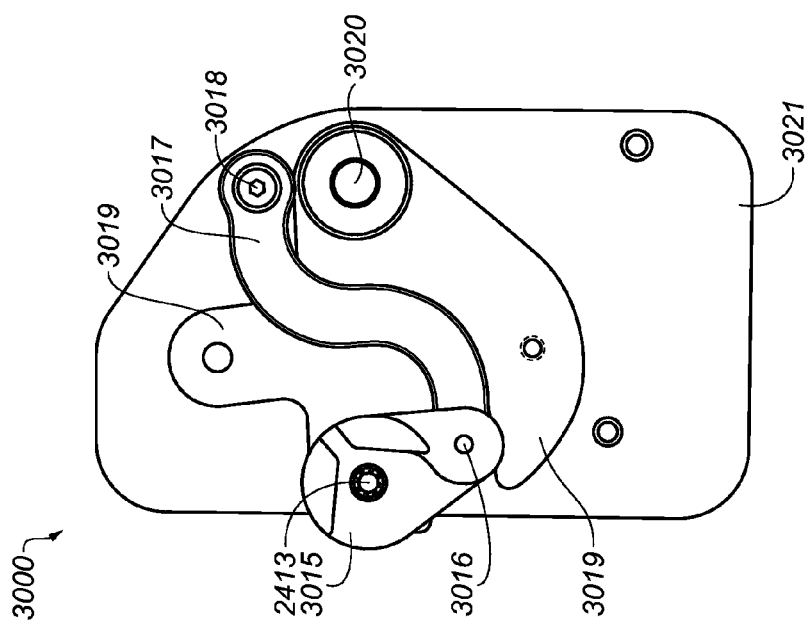

FIGS. 30A-B show the hinge assembly 3000 in a closed position (housing extension 176 fully deployed across the housing gap 38); FIGS. 30C-D show the hinge assembly 3000 in a position between opened and closed; and FIGS. 30E-F show the hinge assembly 3000 in a fully opened position (housing extension 176 fully retracted within housing 2301). As mentioned, the base plate 3021 may be fixedly attached to an interior structure of the housing 2301. Hinge plate 3019 may be rotatably attached to base plate 3021 by hinge pin 3020 and S-link 3017 may be rotatably attached to base plate 3021 by link pin 3018. The traveling and pivoting door support 3015 is rotatably attached to S-link 3017 by a first support pin 3016, and is rotatably attached to the hinge plate 3019 by a second support pin at the traveling pivot axis 2413. Thus, the traveling and pivoting door support 3015 rotates about the traveling rotating axis 2413 while traveling along an arc 3030 (FIG. 30E) centered at the hinge pin 3020. The first support pin 3016 is rotatably connected to the traveling and pivoting door support 3015 and to S-link 3017 and provides the axial force to traveling and pivoting door support 3015 to rotate it about the traveling rotating axis 2413. A sliding disc, or spacer, 3024 (FIG. 30D) may be directly or indirectly attached to a bottom surface of the hinge plate 3019, and travels in contact with and across a top surface of the base plate 3021. The sliding disc, or spacer, 3024 may be made from nylon, another plastic, or other suitable material to minimize sliding friction with the top surface of the hinge plate 3019. A stop post 3025 (FIG. 30F) may be affixed to a top surface of the base plate 3021 to limit movement of the hinge plate 3019.

The base plate 3021 may be used to attach a motor, damping mechanism, or a combination thereof, which, in turn, may be mechanically connected to the hinge plate 3019 to provide a motorized control for opening and closing the housing extension 176, or to provide damping to limit the speed of movement of the housing extension 176. By providing a motive or damping force to the hinge plate 3019 in this manner, the movement of the remaining main components are also controlled, as described herein, due to being directly or indirectly attached to the hinge plate 3019. As described above, the traveling and pivoting door support 3015 is rotatably attached to the hinge plate 3019 by the second support pin at the traveling pivot axis 2413, and is also attached to S-link 3017 by the first support pin 3016.

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

Although sometimes described herein with respect to CBCT digital radiography systems, embodiments of the application are not intended to be so limited. For example, other DR imaging system such as dental DR imaging systems, mobile DR imaging systems or room-based DR imaging systems can utilize method and apparatus embodiments according to the application. As described herein, an exemplary flat panel DR detector/imager is capable of both single shot (radiographic) and continuous (fluoroscopic) image acquisition. Further, a fan beam CT DR imaging system can be used.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An apparatus for cone beam computed tomographic imaging of an extremity of a patient, the apparatus comprising:
 a digital radiation detector and a radiation source each configured to revolve about a central imaging axis whereat at least a portion of the extremity of the patient is positioned to be imaged by the apparatus;
 a C-shaped housing to enclose the source and the detector, the C-shaped housing having a housing gap and a housing extension attached to the housing, the housing extension configured to controllably extend from the housing across the housing gap to enclose the detector as it revolves about the central imaging axis; and means for shielding an interior of the housing from exterior access proximate the housing extension when the housing extension is opened and closed.

2. The apparatus of claim 1, further comprising a hinge mechanism for moving the housing extension across the housing gap and simultaneously rotating the housing extension as it moves into a closed position across the housing gap.

3. The apparatus of claim 2, wherein the C-shaped housing comprises an opening to receive the housing extension when the housing extension is fully deployed, and wherein the means for shielding includes a shield to cover the opening when the housing extension is not fully deployed.

4. The apparatus of claim 1, wherein the means for shielding comprises a fanned blade assembly that extends to shield an interior of the housing when the housing extension is moved to an open position.

5. The apparatus of claim 4, wherein the fanned blade assembly extends in a plane that is parallel to a plane of movement of the housing extension.

6. The apparatus of claim 4, further comprising a manual latch to secure the housing extension in an open position.

7. The apparatus of claim 1, wherein the housing extension is configured to simultaneously travel and pivot as it controllably extends from the housing across the housing gap.

8. The apparatus of claim 1, wherein the housing extension is configured to simultaneously travel and pivot as it controllably extends from the housing across the housing gap.

9. The apparatus of claim 1, wherein the means for shielding comprises a surface of the housing extension when the housing extension is fully deployed.

10. An apparatus for x-ray imaging comprising:
a digital radiation detector and a radiation source each configured to travel about an imaging area where an object is positioned to be imaged by the apparatus;
a housing to enclose the source and the detector, the housing having an open housing gap to allow movement of the object into the imaging area by moving through the open gap, and a housing extension attached to the housing and configured to extend from the housing across the housing gap to close the housing gap and enclose the detector as the detector travels about the imaging area; and
means for shielding an interior of the housing from exterior access proximate the housing extension.

11. The apparatus of claim 10, further comprising a traveling pivot hinge for moving the housing extension across the housing gap and simultaneously rotating the housing extension as it moves into a position to close the housing gap.

12. The apparatus of claim 11, wherein the housing comprises an opening to receive the housing extension when the housing extension is fully extended to close the gap, and wherein the means for shielding includes a shield to cover the opening when the housing extension is not fully extended.

13. The apparatus of claim 10, wherein the means for shielding comprises a fanned blade assembly that extends to shield an interior of the housing when the housing extension is moved to open the gap.

14. The apparatus of claim 13, wherein the fanned blade assembly extends in a plane that is parallel to a plane of movement of the housing extension.

15. The apparatus of claim 14, further comprising an arm attached to the housing and to the fanned blade assembly, the arm biased to extend the fanned blade assembly.

16. The apparatus of claim 10, further comprising a manual latch to prevent the housing extension from moving.

17. The apparatus of claim 10, further comprising a hinge attached to the housing extension, the hinge configured to simultaneously travel and pivot as the housing extension moves across the housing gap.

18. An apparatus for cone beam computed tomographic imaging of an extremity of a patient, the apparatus comprising:
a digital radiation detector and a radiation source each configured to revolve about a central imaging axis whereat at least a portion of the extremity of the patient is positioned to be imaged by the apparatus;
a C-shaped housing to enclose the source and the detector, the C-shaped housing having a housing gap and a housing extension attached to the housing, the housing extension configured to controllably extend from the housing across the housing gap to enclose the detector as it revolves about the central imaging axis; and
a hinge mechanism for moving the housing extension across the housing gap and simultaneously rotating the housing extension as it moves into a closed position across the housing gap.

19. The apparatus of claim 18, wherein the hinge mechanism comprises a traveling pivot hinge configured to simultaneously translate and pivot to move the housing extension across the housing gap and simultaneously rotate the housing extension as it moves into the closed position across the housing gap.

20. The apparatus of claim 19, wherein the housing comprises an opening to receive the housing extension when the housing extension moves into the closed position across the housing gap.

* * * * *